US012808856B2

(12) United States Patent
Cowley et al.

(10) Patent No.: US 12,808,856 B2

(45) Date of Patent: Nov. 24, 2026

(54) MODULAR PROCESS ANALYTICAL TECHNOLOGY TESTING APPARATUS

(71) Applicant: Arranta Bio Holdings, LLC, Watertown, MA (US)

(72) Inventors: Aaron Cowley, Watertown, MA (US); Edita Botonjic-Sehic, Watertown, MA (US); Syed Kaschif Ahmed, Watertown, MA (US); Mark Jandreski, Watertown, MA (US)

(73) Assignee: Arranta Bio Holdings, LLC, Watertown, MA (US)

(*) Notice: Subject to any disclaimer, the term of this patent is extended or adjusted under 35 U.S.C. 154(b) by 0 days.

(21) Appl. No.: 19/426,777

(22) Filed: Dec. 19, 2025

(65) Prior Publication Data

US 2026/0126424 A1 May 7, 2026

Related U.S. Application Data

(63) Continuation of application No. 19/079,849, filed on Mar. 14, 2025.

(Continued)

(51) Int. Cl.
*G01N 33/15* (2006.01)
*G01N 21/05* (2006.01)
(Continued)

(52) U.S. Cl.
CPC ............. *G01N 33/15* (2013.01); *G01N 21/05* (2013.01); *G01N 21/33* (2013.01); *G01N 21/359* (2013.01);
(Continued)

(58) Field of Classification Search
None
See application file for complete search history.

(56) References Cited

U.S. PATENT DOCUMENTS 8,122,849 B2* 2/2012 Clarke ................ G01N 21/359 118/712
2003/0087457 A1* 5/2003 Hughes ................ G01N 33/15 422/534
(Continued)

FOREIGN PATENT DOCUMENTS

CN 1551984 A 12/2004

OTHER PUBLICATIONS

Asachi et al., "Multi-sensors data fusion for monitoring of powdered and granule products: Current status and future perspectives," Advanced Powder Technology, vol. 34: 104055 (2023).
(Continued)

*Primary Examiner* — Jennifer Wecker
*Assistant Examiner* — Tracy Ching-Tian Colena
(74) *Attorney, Agent, or Firm* — KDW Firm PLLC

(57) ABSTRACT

The invention provides a modular apparatus comprising at least one process analytical instrument and a controller adapted for fluid communication with a unit operation of a pharmaceutical or biopharmaceutical manufacturing system, systems comprising the modular apparatus, and related compositions and methods. The modular apparatuses described here and associated digital architecture provide a universal solution to fully integrate any pharmaceutical or biopharmaceutical manufacturing process using a wide range of process analytic tools.

17 Claims, 26 Drawing Sheets

Related U.S. Application Data

(60) Provisional application No. 63/708,332, filed on Oct. 17, 2024, provisional application No. 63/566,133, filed on Mar. 15, 2024.

(51) Int. Cl.

| | |
|---|---|
| ***G01N 21/33*** | (2006.01) |
| ***G01N 21/359*** | (2014.01) |
| ***G01N 21/47*** | (2006.01) |
| ***G01N 21/65*** | (2006.01) |

(52) U.S. Cl.

CPC ............. *G01N 21/47* (2013.01); *G01N 21/65* (2013.01); *G01N 2021/4711* (2013.01); *G01N 2201/0221* (2013.01); *G01N 2201/024* (2013.01); *G01N 2201/126* (2013.01)

(56) References Cited

U.S. PATENT DOCUMENTS

| | | | | |
|---|---|---|---|---|
| 2004/0161852 | A1* | 8/2004 | Anderson | G01N 21/47 436/76 |
| 2008/0008623 | A1* | 1/2008 | Reed | G01N 21/49 422/63 |
| 2010/0118301 | A1 | 5/2010 | Vondras et al. | |
| 2011/0032516 | A1* | 2/2011 | Zhou | G01J 3/02 356/73 |
| 2013/0061657 | A1* | 3/2013 | Nelson | G01N 21/05 250/281 |
| 2015/0198538 | A1* | 7/2015 | Trygstad | G01N 21/3577 702/25 |
| 2016/0018347 | A1* | 1/2016 | Drbal | B01L 3/502707 210/647 |
| 2016/0195564 | A1 | 7/2016 | Hewitson et al. | |
| 2020/0209201 | A1* | 7/2020 | Abolhasani | G01N 21/05 |
| 2023/0287043 | A1 | 9/2023 | Mattila et al. | |
| 2025/0283813 | A1 | 9/2025 | Klishin et al. | |

OTHER PUBLICATIONS

Jorgensen et al., "Advancing non-destructive analysis of 3D printed medicines," Trends in Pharmacological Sciences, vol. 44, No. 6: 379-393 (Jun. 2023).

Potterat et al., "Concepts and technologies for tracking bioactive compounds in natural product extracts: generation of libraries, and hyphenation of analytical processes with bioassays," Natural Product Reports, vol. 30: 546-564 (2013).

Wang et al., "Determination of Iodine Species in Seafood by Ionic Liquid-Based In-line Solid-Phase Extraction-Capillary Electrophoresis," Food Analytical Methods, vol. 12: 2139-2149 (2019).

International Search Report and Written Opinion of the International Searching Authority in International Application No. PCT/US2025/060927 mailed Apr. 7, 2026, 17 pages.

* cited by examiner

MODULAR PROCESS ANALYTICAL TECHNOLOGY TESTING APPARATUS

FIELD OF THE INVENTION

The present invention relates to improvements process analytic technology (PAT) for use in a continuous pharmaceutical and biopharmaceutical manufacturing system.

CROSS REFERENCE TO RELATED APPLICATIONS

This application claims priority to U.S. Provisional Application No. 63/566,133 filed Mar. 15, 2024, and U.S. Provisional Application No. 63/708,332 filed Oct. 17, 2024, the contents of which are hereby incorporated by reference in their entirety.

BACKGROUND

Most biopharmaceuticals are manufactured using batch production methods in which human intervention is required to process a set quantity of material to be produced at the same time. Batch operations may require as long as 1-2 months or more from bioreactor to final formulated product. An alternative approach is continuous manufacturing which is attractive due to its potential to reduce costs while increasing productivity and improving product consistency. Continuous manufacturing processes have been developed in the chemical, petrochemical, food, and mechanical industries. In these contexts, continuous processes have demonstrated less reliance on human labor and fewer gaps in transitioning between unit operations in the process resulting in increased productivity, while the smaller facility footprint required by a continuous process reduces facility costs.

There is a need for continuous manufacturing systems in the biopharmaceutical sector, as an alternative to the more time consuming, resource intensive, and expensive batch processes that represent the current standard of practice, as acknowledged by regulatory agencies which have urged the adoption of continuous biomanufacturing in this sector. See National Academies of Sciences, Engineering and Medicine. *Continuous manufacturing for the modernization of pharmaceutical production.* 2019.

While continuous bioprocessing has yet to be fully realized, several innovations in unit operations have made its implementation more feasible in biopharmaceutical manufacturing. In upstream processing these include developments in perfusion cell culture systems and continuous clarification systems such as continuous centrifugation, alternating tangential flow filtration, and acoustic wave separation. Developments in downstream operations include continuous chromatography and single-pass ultrafiltration and diafiltration capable of achieving high concentration factors and buffer exchange in a single pass of the process material through the module, e.g., in a continuous formulation process.

Despite these and other advances in adapting various unit operations to continuous processing, significant challenges remain in process integration, real-time monitoring and control systems. The present invention addresses the need for improved process analytic technology (PAT) and universal integration to address the needs of a continuous pharmaceutical and biopharmaceutical manufacturing system.

BRIEF SUMMARY

Provided is a customizable, automated, mobile, modular apparatus adapted for performing analytical testing, analysis, and monitoring of a bioprocess in-line or at-line in a biomanufacturing process, and related methods and compositions.

In one aspect, provided is a mobile, modular apparatus for deploying process analytical technology in a pharmaceutical or biopharmaceutical manufacturing process, the apparatus comprising a mobile platform with a weighted base, a control cabinet and an instrument stack disposed within a housing comprising inlet and outlet ports, where the control cabinet includes a human machine interface, a controller, and a data acquisition and analysis software layer and the instrument stack includes two or more process analytical instruments and associated flow cells, tubing and valves, where each of the process analytical instruments is adapted to measure an indication of at least one product attribute from a process fluid flowing through its associated flow cell, where the inlet and outlet ports of the housing connect the flow cells via the tubing in a recirculation loop to a flow path of at least one unit operation of the manufacturing process for in-line data acquisition and analysis, and where the controller and data acquisition and analysis software operate to (i) compare the indication of the at least one product attribute against a predetermined range for the attribute, (ii) determine whether the indication is within the range, and (iii) initiate a first action if the received indication is within the range or a second action if the indication is outside the range. The apparatus may also include where the instrument stack comprises two or more spectroscopic instruments, optionally where the two or more spectroscopic instruments are selected from a Raman spectrophotometer, a mid-infrared (IR) spectrophotometer, a near-IR spectrophotometer, and an ultraviolet-visible (UV-VIS) spectrophotometer. The apparatus may also include where the instrument stack comprises a multiangle light scattering (MALS) detector. The apparatus may also include an internal vessel in the form of a flexible or a rigid container defining an interior space suitable for holding a fluid, where the vessel includes inlet and outlet ports, an optional impeller for fluid recirculation, and an optional probe or sensor. The apparatus may also include one or more environmental protections selected from electromagnetic frequency (EMF) shielding, vibrational dampening, shock absorption, and temperature control. The apparatus may also include at least one sample port or cuvette adapted to be connected to the recirculation loop of the flow path for at-line data acquisition and analysis, for example by a process analytic instrument that does not utilize a flow cell. The apparatus may also include where the recirculation loop connecting the flow cells or cuvette to the flow path of the at least one unit operation includes an external vessel. The apparatus may also include where the recirculation loop is connected via one or more valves to one or more of a material recycle flow path, a waste flow path, and/or a forward processing flow path. The apparatus may also include where the controller comprises an advanced process controller (APC). The apparatus may also include where the external vessel comprises a body in the form of a flexible or a rigid container defining an interior space, inlet and outlet ports, an optional impeller for fluid recirculation, and an optional probe or sensor. The apparatus may also include where the external vessel is a hold vessel, a release tank, a dilution tank, a mixing tank, or a stirred tank reactor. The apparatus may also include where the one or more valves is controlled by operation of the controller in accordance with one or more predetermined criteria. The apparatus may also include where the data acquisition and analysis software layer includes multivariate data analysis, chemometric modeling and/or other advanced process modeling software. Other technical features may be readily apparent to one skilled in the art from the following figures, descriptions, and claims.

Also provided is a pharmaceutical or biopharmaceutical processing system comprising an apparatus as defined herein fluidly coupled to a unit operation of a pharmaceutical or biopharmaceutical manufacturing process in a recirculation loop. The system may also include where the apparatus is fluidly coupled in-line between the unit operation and a second unit operation in the process and the recirculation loop is connected via tubing and one or more valves to one or more of a material recycle flow path, a waste flow path, and/or a forward processing flow path. The system may also include where the apparatus is fluidly coupled in-line between the unit operation and a second unit operation in the process via an external vessel. Other technical features may be readily apparent to one skilled in the art from the following figures, descriptions, and claims.

Also provided is a method for real time release testing in a pharmaceutical or biopharmaceutical process, the method comprising situating an apparatus as described herein in-line or at-line to a unit operation of the process such that the inlet and outlet ports of the apparatus housing connect the flow cells of the apparatus in a recirculation loop to a flow path of the unit operation, recirculating a volume of process fluid from the unit operation through the flow cells of the apparatus, measuring an indication of at least one product attribute from the process fluid via operation of the two or more process analytical instruments of the apparatus, comparing the indication of the at least one product attribute against a predetermined range for the attribute via operation of the data acquisition and analysis software layer of the apparatus, determining whether the indication is within or outside the predetermined range, and executing a first set of instructions via the controller of the apparatus effective to release the volume of process fluid to a second unit operation in the process if the received indication is within the range, executing a second set of instructions via the controller of the apparatus effective to release the volume of process fluid to either a recycle flow path or a waste flow path if the indication is outside the range, or executing a third set of instructions via the controller of the apparatus effective to maintain the volume of process fluid in the recirculation loop until the indication is within the predetermined range. The method may also include recirculating the volume of process fluid into an internal vessel of the apparatus configured with a sample port and one or more probes or sensors of one or more process analytic instruments. The method may also include obtaining a sample of the process fluid from the sample port of the internal vessel for off-line analysis. The method may also include where the sample is obtained via manual or automated sampling. Other technical features may be readily apparent to one skilled in the art from the following figures, descriptions, and claims.

Also provided is a pharmaceutical or biopharmaceutical processing system including a modular apparatus according to any of the preceding embodiments, fluidly coupled between a first unit operation and a second unit operation located immediately downstream from the first unit operation in a biopharmaceutical process.

Also provided is a method for manufacturing a pharmaceutical or biopharmaceutical product that includes integrating a modular apparatus according to any of the preceding embodiments, between one or more unit operations in a batch or continuous processing system. Other technical features may be readily apparent to one skilled in the art from the following figures, descriptions, and claims.

BRIEF DESCRIPTION OF THE SEVERAL VIEWS OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. In the figures, identical or nearly identical or equivalent elements are typically represented by the same reference characters, and similar elements are typically designated with similar reference numbers, with redundant description omitted. For purposes of clarity and simplicity, not every element is labeled in every figure, nor is every element of each embodiment shown where illustration is not necessary to allow those of ordinary skill in the art to understand the disclosure.

To easily identify the discussion of any particular element or act, the most significant digit or digits in a reference number refer to the figure number in which that element is first introduced.

DETAILED DESCRIPTION

Figure 1A:
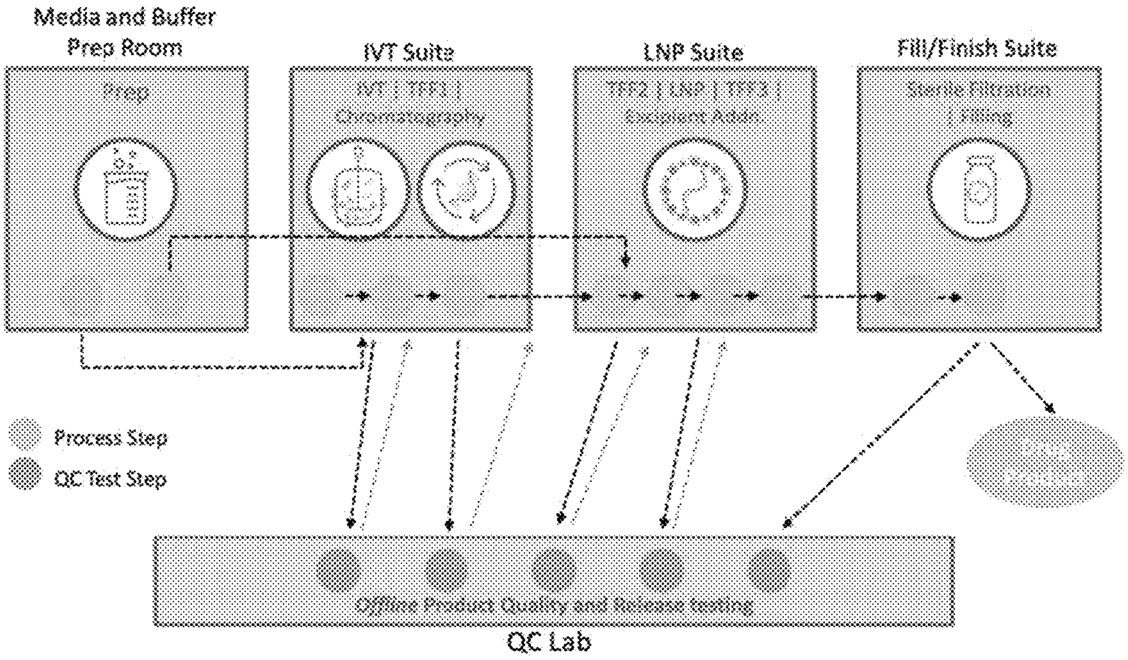
FIG. 1A is a schematic illustrating the inefficiencies of batch processing in biopharmaceutical manufacturing.

The disclosure provides a customizable, automated, mobile, modular apparatus for deploying process analytical technology (PAT) in a continuous biopharmaceutical manufacturing process, referred to herein as a PAT Box apparatus. The apparatus is customizable and modular in terms of its ability to be adapted to monitor different unit operations and be deployed in a "plug and play" fashion at single or multiple locations in a continuous biopharmaceutical manufacturing process. These features allow for customizable real-time data acquisition and monitoring of one or multiple unit operations in the process.

The PAT Box apparatus described herein advantageously combines multiple process analytical technologies into a single contiguous flow path for in-line and/or at-line monitoring of a biomanufacturing process at one or multiple points in the process. The customizable, mobile and compact structure of the PAT Box apparatus obviates the need to configure different analytical technologies in a separate location, such as a cleanroom or distant lab bench. Instead, the PAT Box apparatus consolidates the technologies into a mobile cart where their respective flow cells are arranged into one contiguous flow path for analysis and monitoring. This arrangement significantly increases flexibility in part by providing flow kits adapted for different technologies that can easily be swapped in and out depending on process needs. Process efficiency is enhanced by brining the analytics to the unit operations in-line and/or at-line. Further efficiency improvements are achieved by the decreased sample volumes required for the analytical measurements performed by the consolidated technologies and single flow path of the PAT Box apparatus, particularly where the sensors and/or flow cells are situated in-line in a recirculation loop with the process. Hold-up volumes are also substantially reduced by the ability to bring the apparatus into close proximity with the unit operations. In addition, sample handling is reduced or even eliminated because the PAT Box apparatus can be moved as needed to different unit operations in the process. The reduction in sample handling also reduces contamination risks. Proximity to the unit operations and/or the use of in-line recirculation loops further increases efficiency by substantially reducing the time otherwise needed to remove a sample from the process, transfer it to an analytic instrument or multiple different analytic instruments, and perform associated tasks of sample management, such as manual data entry of sample IDs, forms, etc. Overall, the PAT Box apparatus as described herein provides for the ability to obtain in-process analytics and release test results in real-time to increase process efficiency by reducing both costs and production time. In some cases, where product may be lost due to instability during prolonged processing times using standard methods product quality and yield may also be improved in accordance by incorporation of a PAT Box apparatus into the process as described here.

In one aspect, the PAT Box apparatus comprises a PAT instrument stack and a PAT Control Cabinet. The PAT instrument stack includes in-line instruments and accompanying flow cells, valves, tubing, and pumps, as well as optional probes, cuvettes, and sampling ports that may be utilized, for example, for off-line process analytical technologies. The apparatus also includes electronic connectors adapted to connect the instruments directly to the control cabinet and fluid connectors to connect the flow cells to the process flow path.

The PAT Control Cabinet comprises a human machine interface (HMI), a controller, such as an advanced process controller (APC), and at least four software layers including data acquisition, process scheduling, deviation handling, and real-time execution layers. The data acquisition layer acquires and stores data from the in-line instruments, as well as any optional at-line or off-line instruments. In aspects, the data acquisition layer also functions to close a control loop by communicating with a distributed control system (DCS) or Supervisory Control and Data Acquisition (SCADA) system. In aspects, the data acquisition layer may also report process data to historians and other databases. In aspects, the data acquisition layer may include additional software for performing process modeling such as chemometric modeling and/or other advanced process modeling, for example to process the raw data into product attribute information, which may include for example critical quality attribute (CQA) information or product quality attribute information.

In use, each PAT Box apparatus brings PAT analytics to one or more unit operations in a pharmaceutical or biopharmaceutical manufacturing process enabling product attributes to be monitored, controlled and "released or rejected" for a volume of process fluid at any of several critical control points (CCPs) in the process. The terms product attribute, product quality attribute (PQA), and critical quality attribute (CQA) are used interchangeably herein to refer to a physical, chemical, or biological property or characteristic that should remain within a predetermined limit, range, or distribution to ensure a desired product quality.

In aspects, a PAT Box apparatus is customized for monitoring and control of a particular unit operation in a manufacturing process. A unit operation may include, for example, a bioreactor process, a chromatographic separation process, or a filtration process such as a tangential flow filtration (TFF) process or an ultrafiltration process. The particular unit operation will depend upon the process. For example, unit operations in a monoclonal antibody production process may include a bioreactor, a clarification unit which may be, e.g., a filtration unit such as a depth filtration unit, affinity chromatography, viral inactivation, polishing chromatography using e.g., ion exchange (CEX or AEX) or hydrophobic interaction chromatography (HIC), additional filtration units including diafiltration and sterile filtration, as well as fill and finish units. Similarly for other processes such as plasmid DNA production, adeno-associated virus (AAV) production, and RNA production, the unit operations may include a cell culture bioreactor, a fermentation reactor, or an in vitro transcription (IVT) reactor along with one or more chromatography units and filtration units as well as specialized units such as a lipid nanoparticle formulation (LNP) unit. Accordingly, a PAT Box apparatus as described here may be used in various biopharmaceutical manufacturing processes including processes for manufacture of monoclonal antibodies, antibody drug conjugates, vaccines, including RNA vaccines, RNAi, enzymes, peptides, cell therapies, viral vectors including adeno-associated virus (AAV) vectors and lentivirus vectors, and other gene therapy modalities. In aspects, the manufacturing process is a continuous process. In aspects, the manufacturing process is a continuous process for manufacture of RNA, adeno-associated virus, plasmid DNA, or monoclonal antibodies.

Additional flexibility of the PAT Box apparatus is provided in part by its digital infrastructure which allows for the processing of raw data from various process analytic instruments, which may be in-line, at-line, or off-line, into process-specific product quality attributes. In aspects, the digital infrastructure includes at least one model based on underlying data and assumptions for a particular unit operation. The model may be a mechanistic model or a data-driven model, or a hybrid model that combines aspects of both mechanistic and data-driven models. A mechanistic model refers to a model based on biophysical relationships that have been mathematically elucidated based on a full mathematical understanding of the process and may also be referred to as "white-box models". Data-driven models are mathematical models based solely on the statistical relationships between data, primarily data obtained or derived from online sensors and offline analysis. Data-driven models are not based on biophysical relationships and may also be referred to as "black-box models." Hybrid models combine mechanistic and data-driven models. The digital infrastructure may also include algorithms to measure the relationship between variables using correlation analysis which relies on establishing correlations between sensor signals, process parameters, and quantity and quality parameters which may be measured offline. For example, the extent of the linear relationship is determined using a Pearson's correlation. Other methods are available to measure nonlinear relationships, for example, Spearman's rank correlation, which is a nonparametric measure of rank correlation reporting the statistical relationship between the rankings of two variables. In aspects, the digital infrastructure may include algorithms for carrying out one or more statistical methods selected from multiple linear regression (MLR), partial least squares regression (PLS), structured additive regression (STAR), random forest (RF), support vector machines regression (SVM), neural networks (NNs), deep learning (DL), and Gaussian process regression (GPR).

Accordingly, also provided are methods for the design, optimization, monitoring, and control of a biopharmaceutical manufacturing process utilizing a PAT Box apparatus as described herein, as well as related systems incorporating at least one PAT Box apparatus.

In an aspect, provided are methods for designing and/or optimizing a biopharmaceutical manufacturing process utilizing one or more PAT Box apparatuses as described herein to identify critical control points (CCPs) in the process, i.e., the critical unit operations at which product quality attributes should be monitored for real-time testing and release at each unit operation.

In an aspect, provided are methods for monitoring and controlling a biopharmaceutical manufacturing process utilizing one or more PAT Box apparatuses as described herein, the methods comprising continuous monitoring and control of one or more CQAs in a process stream by operation of a PAT Box apparatus as described herein.

In an aspect, provided are methods for real-time monitoring, testing, and release of a product stream at one or more defined points in a biopharmaceutical manufacturing process, which method may also be referred to as real time release testing (RTRT), the methods comprising monitoring, testing and release by operation of a PAT Box apparatus as described herein.

The advantages of the PAT Box apparatus described here include optimizing a biopharmaceutical manufacturing process for continuous operation via monitoring and control of one or more unit operations in the process. FIG. 1A illustrates the disadvantages of batch processing where at least several analytical assays must be conducted in an off-line setting. This requires samples to be removed from the batch process and stored until data is collected and a determination is made as to whether quality control (QC) standards are met or not. Process steps are gated by QC release. This creates inefficiencies due to the need to transfer and test samples taken at various points in the process and hold until QC release. This is illustrated in the figure by dashed lines which represent the broken progression of a biopharmaceutical product along the production line due to the need to wait for off-line QC testing results in order to move forward. In addition, limited in-process information is obtained, increasing risk that the manufacturing process may need to be reworked.

Figure 1B:
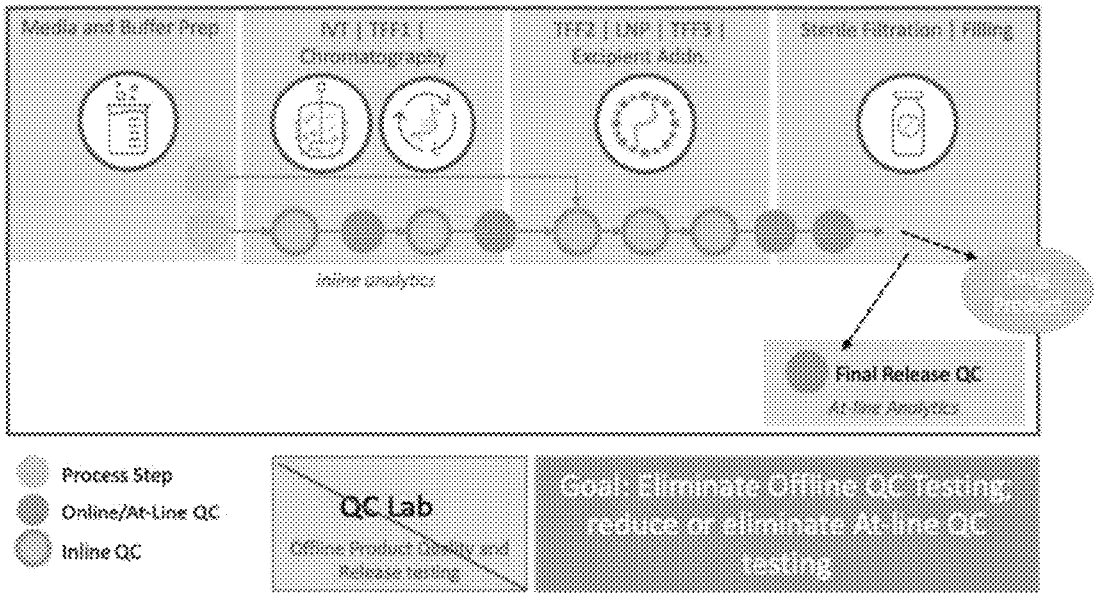
FIG. 1B is a schematic illustrating the advantages of a continuous biomanufacturing process.

FIG. 1B illustrates a continuous biomanufacturing process in which QC testing occurs during the process, for example using a PAT Box apparatus as described herein. Solid lines in the figure illustrate the uninterrupted progression of product along the production line. Continuous manufacturing has several advantages including uninterrupted manufacturing whereby QC results are fed to automated control software allowing for constant monitoring and real-time product characterization, and all processes and QC testing occur in a single cleanroom suite. Generally, utilizing a continuous process, product can be produced over 24-48 hours compared to on the order of 2 or 3 months for a batch process.

Figure 2:
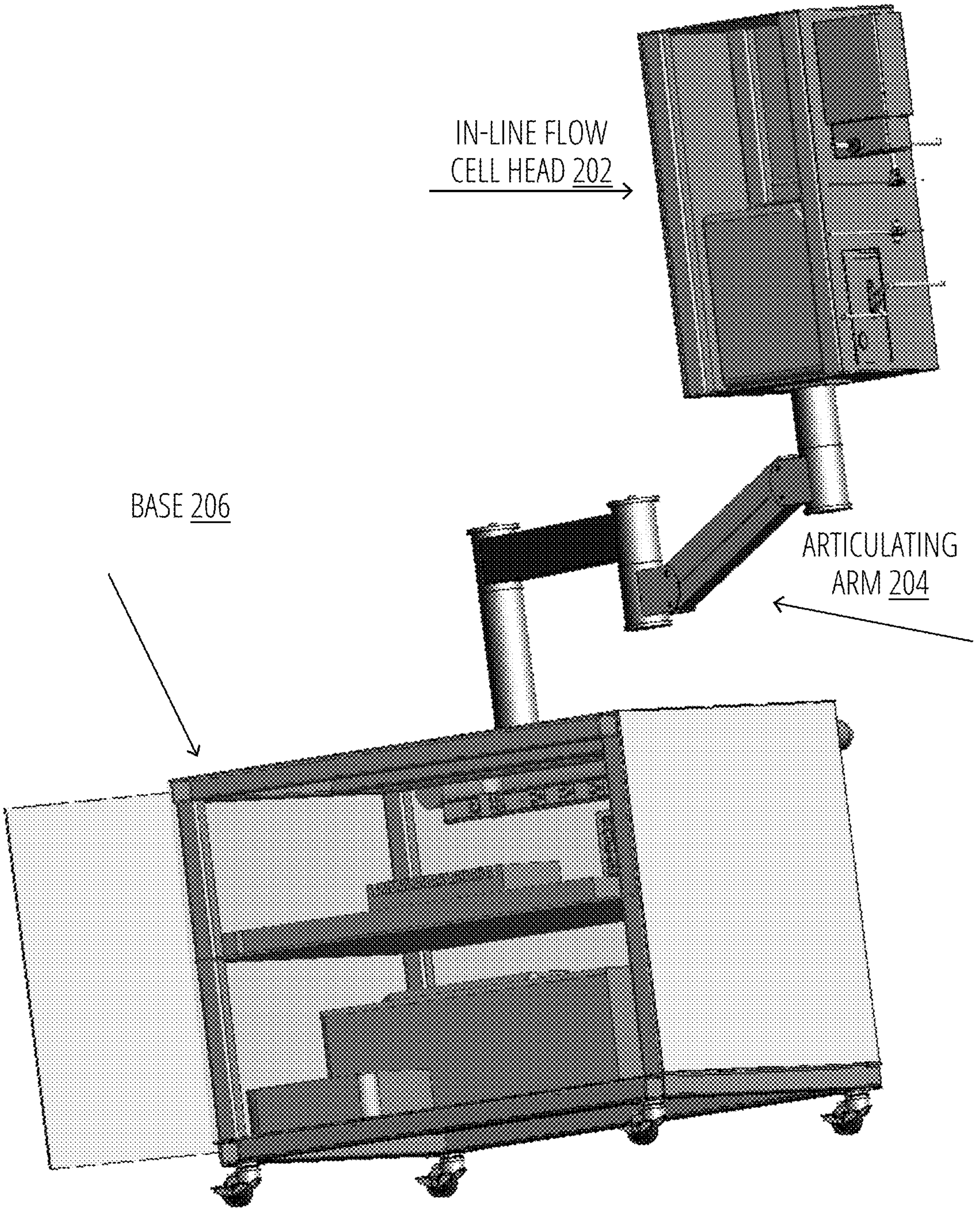
FIG. 2 is a schematic illustrating an embodiment of a PAT Box apparatus.

FIG. 2 illustrates an embodiment of a PAT Box apparatus where a weighted base 206 houses the PAT Control Cabinet and the PAT instrument stack. An articulating arm 204 connects the weighted base to an in-line flow cell head 202 containing a set of flow cells customized for process-specific in-line instruments and their respective transmitters. The PAT instrument stack contains the in-line instrument computers. The PAT Control Cabinet contains electrical I/O, and optionally a programmable logic computer (PLC). The control cabinet may also contain an ethernet switch for connecting to a manufacturing network and/or a digital control infrastructure that may include e.g., a digital twin, a simulator, process models, and a Knowledge Hub which may integrate facility data with process data, including historical process data and clinical data, as well as data from the digital twin and/or simulator. The PAT Box apparatus may also include tubing, valves and pumps configured to control the flow of process fluid between an external vessel, a unit operation, and/or a recirculation loop and the flow cells. In operation, one or more valves and/or pumps may be controlled by a controller of the PAT Control Cabinet. The PAT Box apparatus may also include fluid inlet and outlet ports, additional ports for sensors and/or probes and one or more sample ports. Also provided is a system including a PAT Box apparatus and associated mechanical and digital infrastructure.

The in-line flow cell head 202 is adapted to add or remove flow cells as needed to customize the PAT Box apparatus for use with a particular unit operation. The flow cell head may also include one or sample ports and/or cuvettes. This versatility allows for the incorporation of data from a variety of different in-line, at-line, and off-line process analytical instruments. Exemplary process analytical instruments may include spectrophotometers, refractometers, dynamic light scattering instruments, nuclear magnetic resonance (NMR) instruments, liquid chromatography-mass spectroscopy instruments (LC-MS), and the like. Thus, in one aspect, the PAT Box apparatus may be configured to measure and process data from one or more spectroscopic instruments, such as instruments for detecting Raman, infrared (IR), and ultraviolet (UV) spectra. In another aspect, the PAT Box apparatus may be configured to measure and process data from both a spectroscopic instrument and one or more additional instruments such as a refractometer for measuring refractive index (RI), and/or a dynamic light scattering (DLS) instrument, e.g., for measuring multiangle light scattering (MALS), which may also be referred to as a MALS detector. In an aspect, the PAT Box apparatus is configured to support an at-line process analytical instrument, optionally wherein the at-line process analytical instrument is a high performance liquid chromatography (HPLC) instrument, a flow cytometer, a capillary electrophoresis (CE) instrument, a mass spectrophotometer, an osmometer, a UV-VIS spectrophotometer, a fluorometer, a light scattering detector, or a luminometer.

The articulating arm advantageously brings the in-line flow cells close to the unit operation or vessel in the biomanufacturing process. In some aspects, a recirculation line may be used to pull process material from the unit operation for passing through the in-line flow heads, sensors, and/or probes of the head 202. Use of an articulating arm allows for a shorter recirculation line and smaller hold-up volumes in the line compared to what would be required if the apparatus was located at a more distant site from the unit operation. The articulating arm also allows for optimal positioning and increased mobility around the manufacturing equipment while decreasing the overall footprint needed for the PAT Box apparatus.

Some configurations of the PAT Box apparatus may require fewer process analytic technologies or technologies that have smaller components. Combined with an articulating arm, this may create an unstable top-heavy configuration unless properly mitigated with a weighted base. Thus, the weighted base provides an additional functional enhancement to increase safety to equipment and personnel.

In addition, some configurations of the PAT Box apparatus may include built-in environmental protections such as electromagnetic frequency (EMF) shielding, vibrational dampening, shock absorption, and temperature control. For example, where the PAT Box apparatus includes a Mid IR and NMR component, EMF shielding can be utilized to protect the instrument from interference that could cause failure or inaccurate measurement. As another example, where a PAT Box apparatus includes a DLS component, vibrational dampeners and shock absorbers may be included. Temperature control strategies may include one or more air fans or liquid cooling using convective heat transfer.

In aspects, the weight base comprises an automated leveling system.

Figure 3:
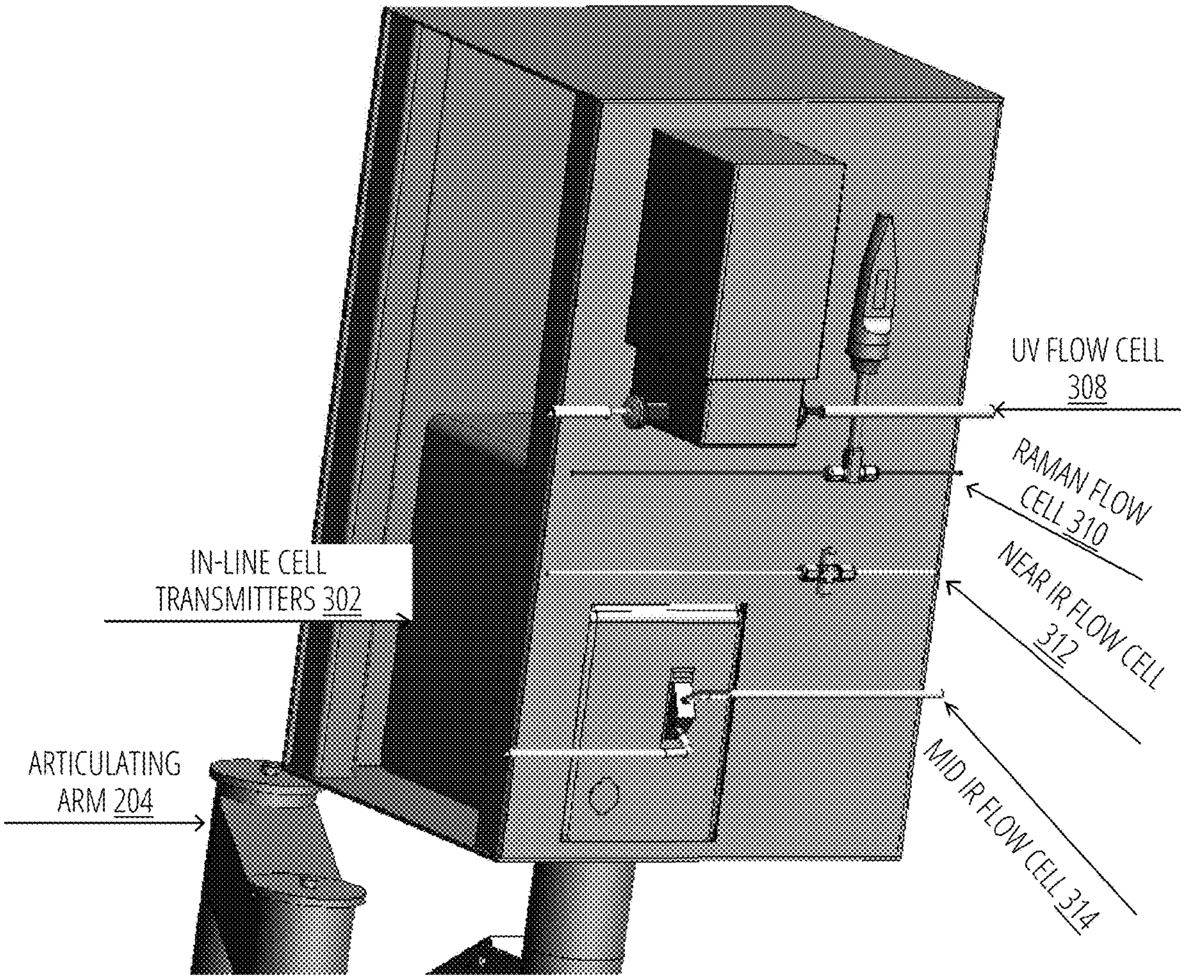
FIG. 3 is a schematic illustrating an embodiment of an in-line flow cell head of a PAT Box apparatus.

FIG. 3 is an inset of the in-line flow cell head 202 showing exemplary flow cells, a UV flow cell, a Raman flow cell, a Near IR flow cell, and a Mid IR flow cell, secured to the flow cell head. The interior of the head contains any necessary transmitters for the in-line flow cells. This configuration allows for the flow cells to be positioned close to a unit operation or vessel recirculation loop for fluid connection in-line to the biomanufacturing process.

In aspects, the PAT Box apparatus may be configured to measure and process data from one or more of a spectrophotometer, a refractometer, a multiangle light scattering (MALS) detector, and/or a DLS instrument. In aspects, the spectrophotometer may detect Raman spectra, including Fourier Transform Raman Spectroscopy (FR-Raman), infrared (IR), including mid-IR (MIR), near-IR (NIR), far-IR (FarIR), or ultraviolet (UV) spectra and/or visible (VIS) wavelengths. In aspects, the spectrophotometer may also include an ion mobility spectrophotometer (IMS).

In aspects, the instrument stack of the PAT Box apparatus includes two or more spectroscopic instruments selected from a Raman spectrophotometer, a mid-infrared (IR) spectrophotometer, a near-IR spectrophotometer, and an ultraviolet-visible (UV-VIS) spectrophotometer.

In aspects, the instrument stack of the PAT Box apparatus includes a Raman spectrophotometer, a mid-infrared (IR) spectrophotometer, a near-IR spectrophotometer, and a UV-VIS spectrophotometer. In aspects, the PAT Box apparatus includes a Raman spectrophotometer, a mid-infrared (IR) spectrophotometer, a near-IR spectrophotometer, a UV-VIS spectrophotometer and a multiangle light scattering (MALS) detector.

In aspects, the instrument stack of the PAT Box apparatus includes a refractometer.

In aspects, the instrument stack of the PAT Box apparatus includes an ion mobility spectrophotometer (IMS).

In aspects, the instrument stack of the PAT Box apparatus includes a nuclear magnetic resonance (NMR) instrument.

Figure 4:
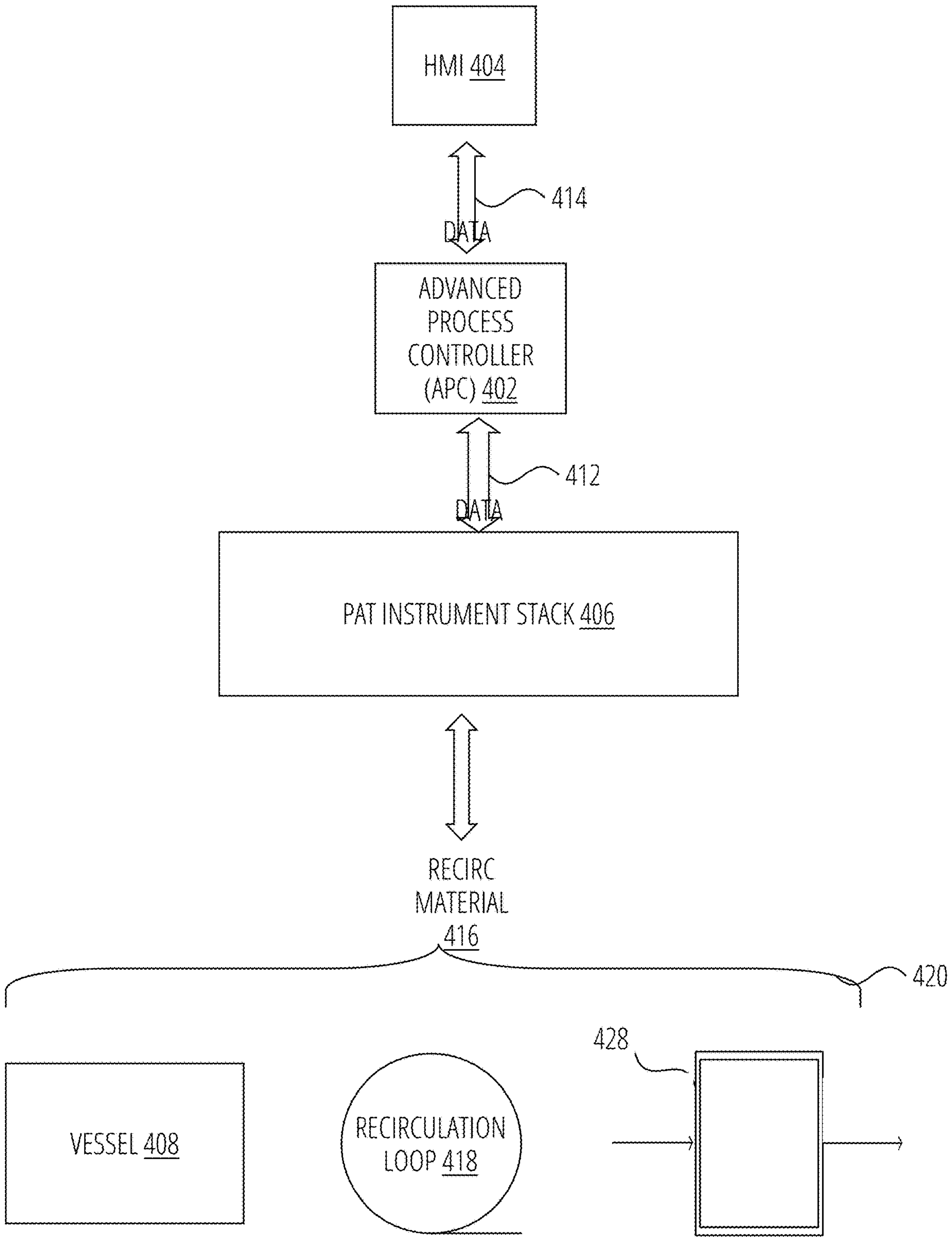
FIG. 4 is a schematic showing the flow of data and process material between a PAT Box apparatus and a vessel, recirculation loop, or other process equipment, in accordance with one embodiment.

FIG. 4 schematically illustrates the flow of data and process fluid in accordance with different aspects of a PAT Box apparatus in operation. Shown are the HMI 404 and controller, e.g., an Advanced Process Controller (APC) 402 of the PAT Control Cabinet. Also illustrated is the flow of data between these two elements and the PAT Instrument Stack 406. Also shown is the flow of process fluid as Recirc Material 416 between the flow cells, sensors, and/or probes of the PAT Instrument Stack 406 and an external vessel 408, a recirculation loop 418, or a unit operation 428.

In an illustrative example of real time release testing (RTRT), the vessel 408 may be fluidly connected with a process stream between a first unit operation and a second unit operation in a biopharmaceutical manufacturing process. In operation, a volume of the process stream enters the vessel 408 from the first unit operation and recirculates between the vessel and the flow cells, sensors and/or probes of the PAT Box apparatus while data is obtained. Data obtained from the PAT instruments is analyzed by the (APC) 402 operating in conjunction with an appropriate model to determine if the product stream satisfies a predetermined criteria, which may relate to, for example, a CQA of the product. If the criteria is satisfied, the controller executes a set of instructions to release the volume of process fluid to the second unit operation in the process.

The HMI may include a digital display comprising a dashboard including a visual output of model results and an interface for control of individual sensors and probes. In aspects, the HMI is in the form of a computer, for example a laptop computer or a programmable logic computer (PLC).

As discussed above, in aspects, the controller may include at least four software layers. The at least four software layers include a data acquisition layer, a process scheduling layer, a deviation handling layer, and a real-time execution layer. In aspects, the software layers execute a set of programmable instructions. In aspects, the programmable instructions may be programmed in a language selected from C, Python Java, JavaScript, Perl, Tcl, or Smalltalk.

In aspects, the controller includes a distributed control strategy (DCS) system including a host computer performing optimization algorithms and advanced control strategies and one or more proportional integral derivative (PID) controllers performing device level controls. The system may also include control units performing regulatory level control functions, such as PID algorithms, and may also include data gathering and extraction capabilities. The system may also include data storage devices to store process data for control and process analytics. Also included is software to communicate and interact with controllers, inputs, and outputs.

In aspects, the APC and HMI may be situated in a cabinet physically separated from the PAT Instrument Stack 406.

Figure 5:
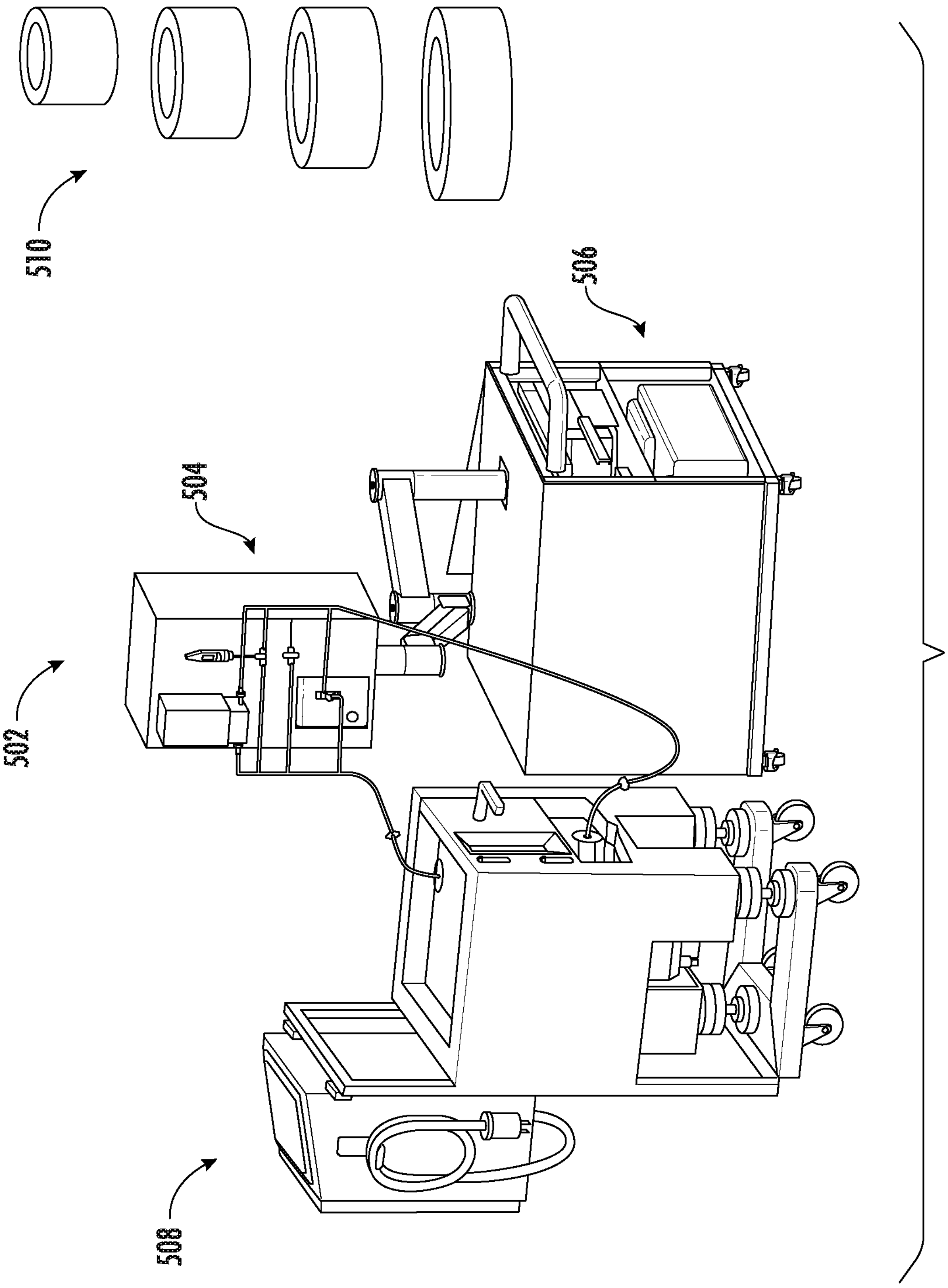
FIG. 5 is a schematic of a PAT Box apparatus in accordance with one embodiment, showing connection to an external vessel which may be, e.g., a release tank, a hold tank, or a dilution tank.

FIG. 5 illustrates a configuration of a PAT Box apparatus 502 situated next to an external vessel 508 which may be connected to a unit operation of a manufacturing process, or may be situated in-line between two unit operations of the process. The figure illustrates tubing connecting the flow cells of the head 504 to the external vessel. In other aspects, where the external vessel is absent, the tubing may connect directly to a unit operation of the process. The external vessel may be any type of vessel, tank or bag. The external vessel may include a plurality of ports, including IO ports for data transfer between multiple control panels and/or software. In aspects, the external vessel incorporates one or more analytical detectors, sensors and/or probes including for example, a conductivity sensor, a temperature sensor, and/or pH probe. The external vessel may have a volume of from 0.100 to 5000 liters, from 0.500 to 1000 liters, or from 2 to 500 liters.

Flow Kits

In an advantageous aspect of its versatility and modularity, a PAT Box apparatus may be configured with a custom set of flow cells and optional sensors or probes, along with associated tubing and valves adapted for a particular set of process analytic instruments to meet the needs of a particular manufacturing process. The set of flow cells, tubing, valves and optional sensors or probes adapted for a specific use may be referred to herein collectively as a flow kit.

The tubing accompanying a flow kit may be adapted for various purposes such as temperature control and/or flow rate. In aspects, the temperature control capabilities may derive from insulated tubing and/or a jacketed stainless steel tube with temperature control fluid. In the latter context, the outer tube flows temperature controlled fluid that is regulated by a temperature control unit (TCU). The inner tube contains the product flow stream and temperature control fluid passes around the product flow stream thereby transporting heat towards or heat away from the product flow stream via convection. The temperature control fluid that transports heat towards or away from the product flow stream then returns to the TCU to be refreshed towards the temperature set-point. This aspect may be useful, for example, where product is temperature sensitive and/or temperature variation can cause fouling of the tubing or sensors.

The tubing accompanying a flow kit may also or alternatively be adapted to produce a particular flow rate through the flow cell(s). In FIG. 5, the inset 510 illustrates the wide range of flow rate capabilities that may be obtained using tubing having various different inner diameters. For example, specific flow rates, pressure profiles, or Reynolds number conditions can be attained inside the tubing or flow cell by either increasing or decreasing the flow rate via the in-line flow cell tubeset pump, and/or by increasing or decreasing the tubing inner diameter. In aspects, the flow rate may range from 0.0-50.0 L/min and the inner diameter of the tubing may range from 1/32 inch to 1/2 inch. In aspects, the inner diameter of the tubing may be 1/32 inch, 1/8 inch, 1/4 inch, or 1/2 inch.

Also provided are additional flow kits including a calibration flow kit. The calibration flow kit is used to calibrate in-line flow cell instrumentation and/or validate the operational and performance of the in-line flow cell instruments. For example, a Raman in-line flow cell may need to be tested to confirm the laser intensity is within range and the spectral readings are sending back the range and intensity as expected for a certain reference standard such as ethanol. This calibration activity might be performed before first use, such as during an installation, operation, and/or performance qualification or for routine preventative maintenance activities. After completion of calibration or validation activities, the calibration flow kit may be removed and replaced with a process flow kit.

Also provided is a cleaning in place (CIP) flow kit. Where in-line flow cells are permanently attached to their internal components or instrumentation and cannot be made single use, the flow cells may need to be cleaned and sanitized, either before use or after becoming fouled. The CIP flow kit includes "Y" connectors upstream and downstream of the flow cells so that cleaning solution can flow through the flow cells.

Figure 6:
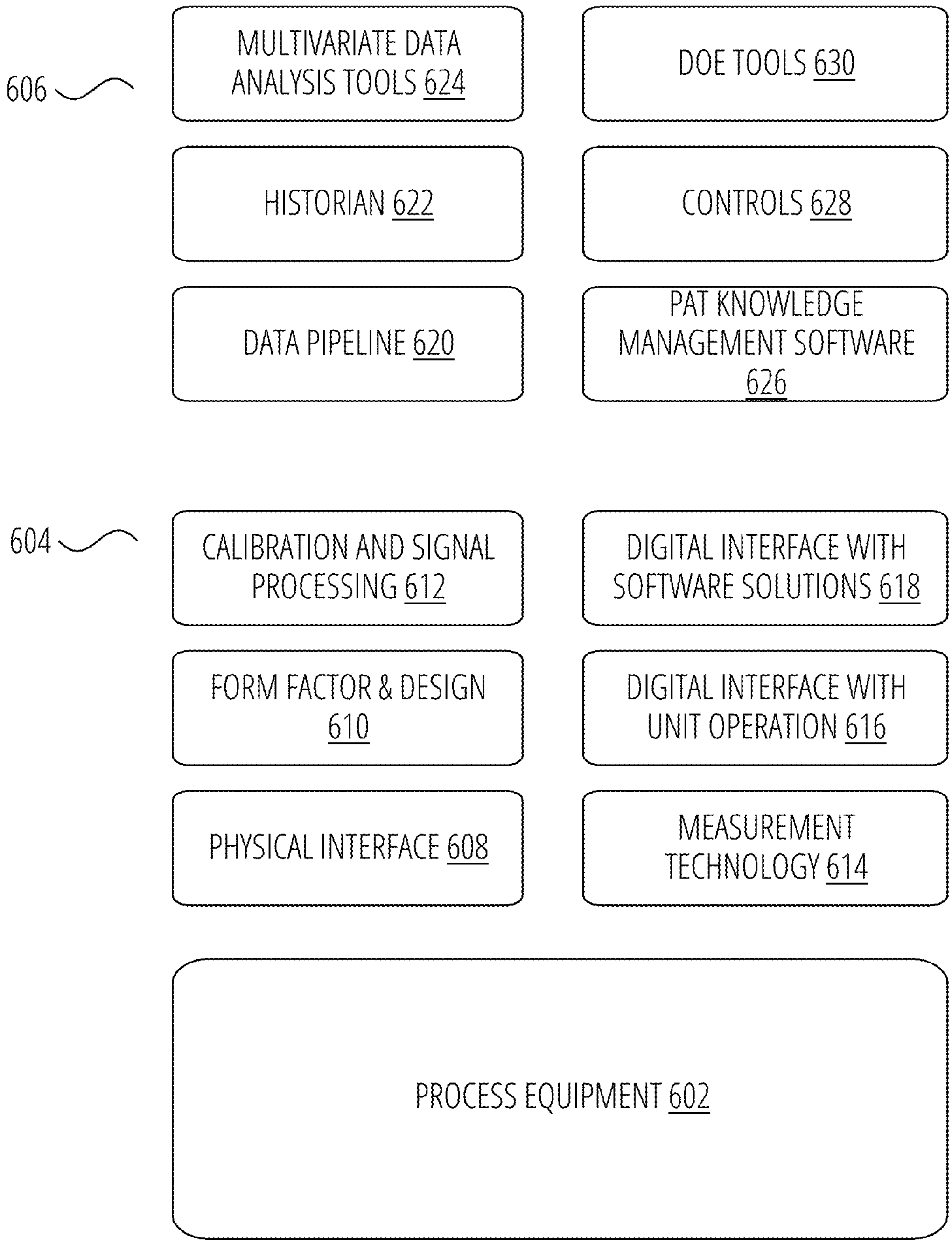
FIG. 6 is a schematic illustrating the modular framework of the PAT Box apparatus.

FIG. 6 schematically illustrates an embodiment of a PAT Box apparatus as described herein. The figure illustrates the modular framework of the apparatus. Shown is the PAT instrument stack 604 and the PAT Control Cabinet 606 of the apparatus which integrate with process equipment 602.

The PAT Control Cabinet includes communications, data, and analysis (CDA) software. In aspects, the PAT Control Cabinet includes computational modeling 624 software such as multivariate data analysis tools 624 which permit real-time insight and response via accessible/static and dynamic model building. In aspects, also included is design of experiments (DOE) software, a historian 622, process controls 628, and a data pipeline 620. Also included is PAT Knowledge Management software 626 which provides automated data collection, extraction, harmonization and storage as well as multivariate data analysis (MVDA) capabilities, technology transfer and batch record integration. In aspects, an application programming interface (API) adapter may be included to integrate with existing in-line or at-line process analytic instruments. In operation, the PAT Knowledge Management software 626 processes raw data, including using available models as needed to convert the data, e.g., spectra, into appropriate product attributes, including critical quality attributes (CQAs). In aspects, software tools of the PAT Control Cabinet provide easy to understand outputs having clear direction that may be integrated into process controls.

The PAT instrument stack 604 includes various modules adapted to be quickly integrated into a manufacturing process in a "plug and play" fashion. In aspects, the modules include a physical interface 608 with the process equipment. In aspects, the interface is fully integrated with a single-use system comprising single use pre-calibrated consumables in a closed, sterile system. Another module includes scalable in-line and on-line process measurement technologies 614 which measure CCPs and CQAs for process control and release testing. Also included is a calibration and signal processing 612 module. In aspects, the calibration and signal processing 612 module is pre- or auto-calibrated. In aspects, the calibration and signal processing 612 module includes straightforward calibration workflows not disruptive to the process and/or where limited recalibration is required.

In aspects, the PAT Box apparatus may track in real-time the progress of a process and transmit data until a desired optimization is reached or the process terminates.

In aspects, the PAT Box apparatus is configured to control upstream and downstream unit operations via included compatibility with industry standard systems including, for example, Delta V™, Ignition™, Unicorn™, Wonderware™, MFCS™, and OPC-UA™. In aspects, the PAT Box apparatus controls upstream and downstream unit operations based on analytical results gathered by all process analytic instruments, e.g., in-line, at-line, on-line, and off-line.

Figure 7B:
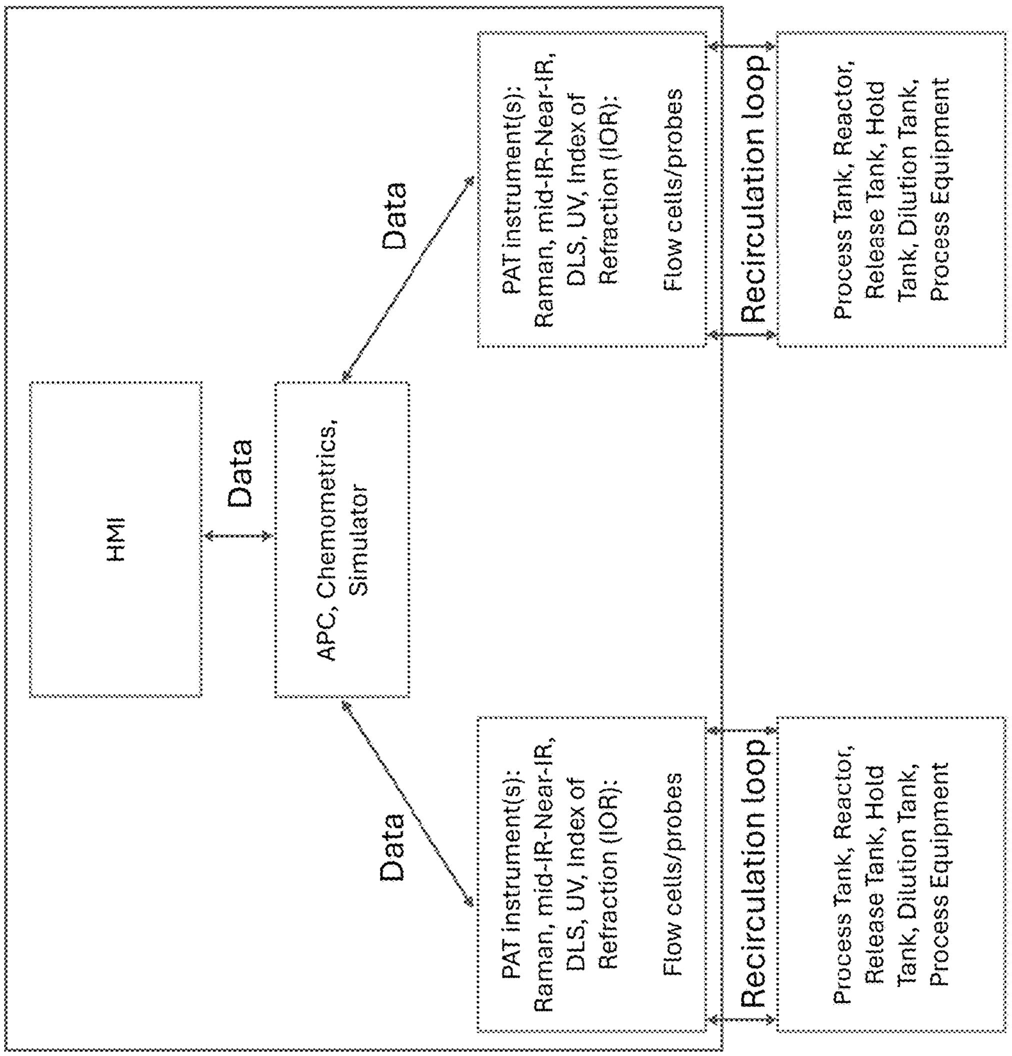
FIG. 7B is a schematic showing data flow between the HMI and APC of the PAT Control Cabinet with two PAT instrument stacks each connected to a different unit operation or vessel.
Figure 7A:
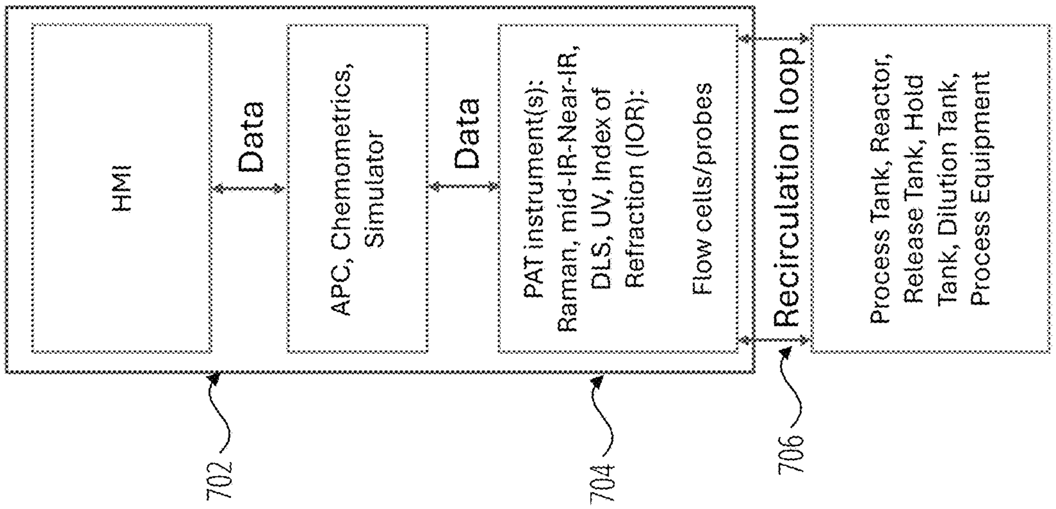
FIG. 7A is a schematic showing data flow between the HMI and APC of the PAT Control Cabinet with the PAT instrument stack containing instruments and associated flow cells, probes, etc. Also depicted is the flow of process fluid in a recirculation loop between the PAT instrument stack and a unit operation such as a reactor or other process equipment, or a vessel, such as a release tank, a hold tank, or a dilution tank.

FIG. 7A schematically illustrates PAT Control Cabinet 702 including a human machine interface (HMI), a controller, depicted as an advanced process controller (APC), and software layers including a data acquisition layer that acquires and stores data from the in-line and at-line instruments, as well as any optional off-line instruments. In aspects, the data acquisition layer also functions to close a control loop by communicating with a distributed control system (DCS) or SCADA system. In aspects, the data acquisition layer may also report process data to historians and other databases. In aspects, the data acquisition layer may include additional software for performing process modeling such as chemometric modeling and/or other advanced process modeling, for example to process the raw data into product quality attribute information.

Also illustrated is a PAT instrument stack 704 including one or more analytic instruments and associated flow cells and probes. Exemplary flow cells that may be included are a Raman flow cell, a UV/VIS flow cell, a mid-IR flow cell, a near-IR flow cell, a DLS flow cell, and an index of refraction (IoR) flow cell, as described in more detail infra.

As illustrated, the PAT Box apparatus is in fluid communication via a recirculation loop 706 with, e.g., a unit operation of a pharmaceutical or biopharmaceutical manufacturing process, or an external vessel such as a process tank, a release tank, a hold tank, a mixing tank or a dilution tank, as described in more detail infra.

FIG. 7B schematically illustrates an embodiment where two PAT Box apparatuses are connected via an electronic feedback loop to a PAT Control Cabinet where the HMI is configured for two-way communication with the instruments of the PAT instrument stack. As depicted here, each set of analytic instruments is in fluid communication via a recirculation loop with a unit operation, which may be e.g., a bioreactor, a chromatography apparatus, a filtration apparatus, etc., or a process vessel, which may be e.g., a hold tank, a mixing tank, etc.

Figure 8:
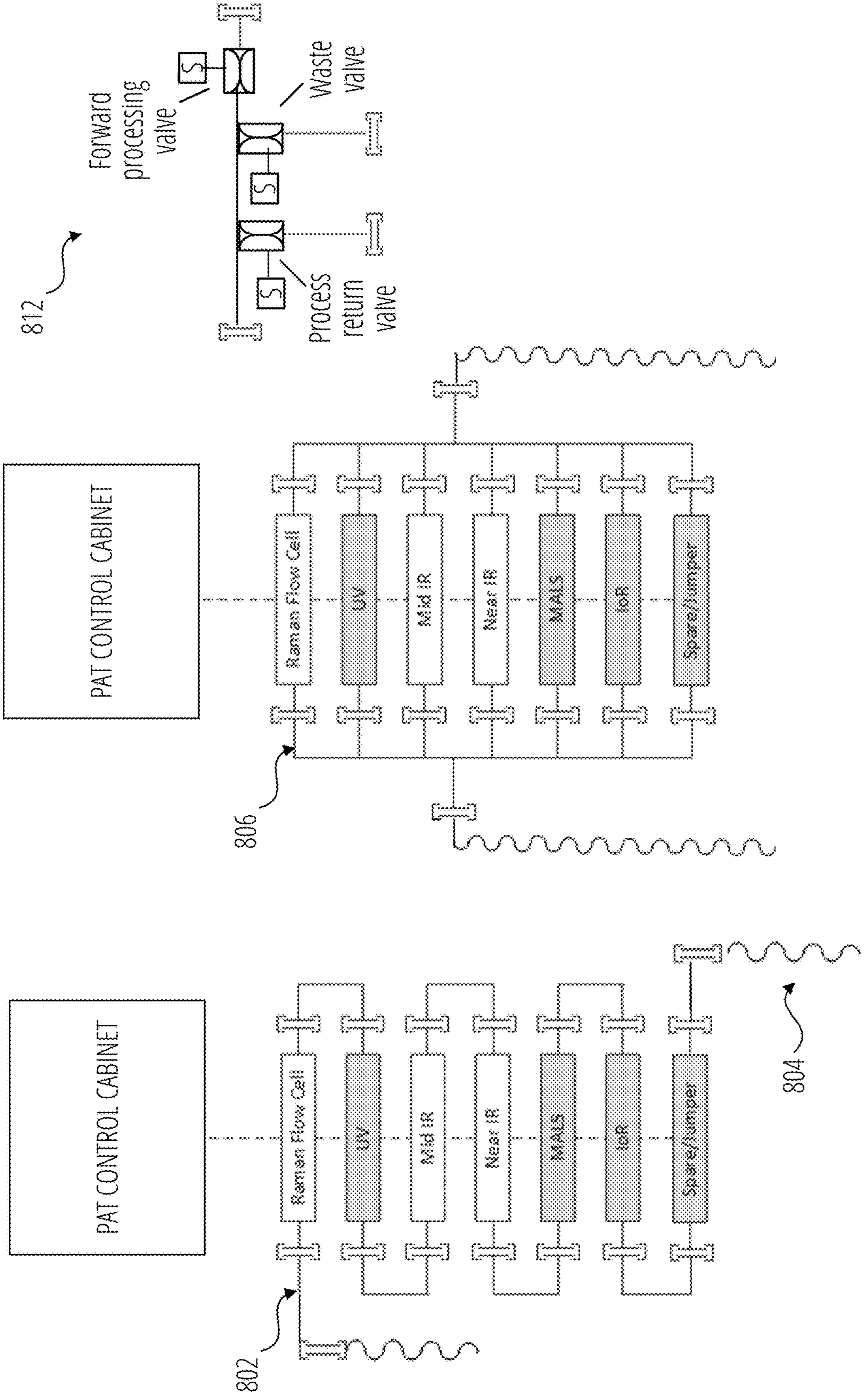
FIG. 8 is a schematic illustration in accordance with one embodiment showing flow cells of the PAT Box apparatus in a series and parallel configurations.

FIG. 8 is a schematic illustration of the flow cells of the PAT instrument stack. The flow cells may be arranged either in series (left) or in parallel (right) in relation to the flow path, depending on the needs of the end-user. For example, flow cells connected in series allow for a "plug and play" configuration in which additional flow cells may be added end to end on the string of PAT flow cells, as needed. This configuration occupies a larger footprint compared to flow cells configured in parallel. Flow cells configured in parallel occupy a smaller footprint, but are somewhat less flexible than a series configuration because flow cell tubesets and/or piping need to be preconfigured.

The schematic illustrates exemplary flow cells that may be included in a flow kit. These include a Raman flow cell, a UV/VIS flow cell, a mid-IR flow cell, a near-IR flow cell, a multi-angle light scattering (MALS) instrument flow cell, and an index of refraction (IoR) flow cell. In an aspect, the UV/VIS flow cell is a variable pathlength flow cell such as a FlowVPX® flow cell available from Repligen Corp.

The provision of customized flow kits suitable for different production modalities highlights the versatility of the PAT Box apparatus. Different production modalities, such as RNA, DNA, monoclonal antibody, viral vector, etc., may require different technologies to measure relevant product criteria, including product quality attributes. When comparing testing methods between modalities, there are some technologies that measure product attributes for multiple modalities and some than can only measure product attributes for a single modality. For example, some forms of spectroscopy can measure both RNA concentration and protein concentration. However, a MALS device may be able to measure lipid nanoparticle size for an RNA production line, but it may not be able to measure any product attributes for a monoclonal antibody process.

This problem is addressed by the provision of a plurality of modular flow kits, each adapted to a production modality. The modular flow kits are adapted for ease of replacement such that one may be easily removed and replaced with another. This allows for a single PAT Box apparatus to be utilized for multiple different modalities of production. For example, where the modality is RNA production, the flow kit may include RNA specific flow cells such as Mid IR, Near IR, and MALS. In another example, where the modality is antibody production, the flow kit may include protein specific flow cells such as IoR, DLS, FT-IR, and fluorescence.

Accordingly, in aspects, a flow cell tubeset may be provided as a flow kit for installation in a PAT Box with in-line process analytical instruments in a series or parallel flow path configuration along with associated tubing, valves, and connectors. In one aspect is provided a single use flow kit where the flow cells are arranged either in series or in parallel. For example, in FIG. 8, the flow cells in white, Raman, MidIR, and NearIR, may be supplied as a single use flow kit including single-use tubing, connectors, and flow cell components. Not all components may be single use and may need to be removed from the flow kit after use for cleaning and/or sanitization.

In another aspect, provided is a single use flow kit with smart waste and release valves where the flow cells are arranged in either a series or parallel configuration and the kit includes associated tubing, valves, and connectors. In accordance with this aspect, provided are multiple outlets connecting to single use "smart" pinch valves for waste and forward processing. In an aspect, single use tubing is placed into permanent pinch valves for use during processing. Once the batch is complete, the flow kit is removed from the holders (not shown) and pinch valves are discarded. In an aspect, the pinch valves may be automated solenoid pinch valves.

In another aspect, provided is a single use flow kit with smart return, waste and release valves where the flow cells are arranged in either a series or parallel configuration and the kit includes associated tubing, valves, and connectors. In accordance with this aspect, provided are multiple outlets connecting to single use "smart" pinch valves for process return material, waste, and forward processing. The single use tubing is placed into permanent pinch valves for use during processing. Once the batch is complete, the flow kit is removed from the holders (not shown) and pinch valves and discarded.

Shown as an inset in FIG. 8 is an exemplary configuration of a smart valve set 812 including a process return valve, a waste valve, and a forward processing valve. In aspects, these valves may be automated solenoid pinch valves. See FIG. 12A and FIG. 12B for exemplary configurations of such a valve set.

The flow cells of the PAT instrument stack may be fluidly connected to one or more unit operations and/or vessels via suitable connectors 806 and tubing 804. In aspects, the tubing 804 may be flexible tubing. The flow cells and flexible tubing can be connected to each other and unit operations via any suitable connector. Suitable connectors include, for example, sanitary tri-clamp connectors, hose barb connectors, tube compression connectors, quick connects, aseptic connectors, or other standard connectors used in the biopharmaceutical industry.

Figure 9:
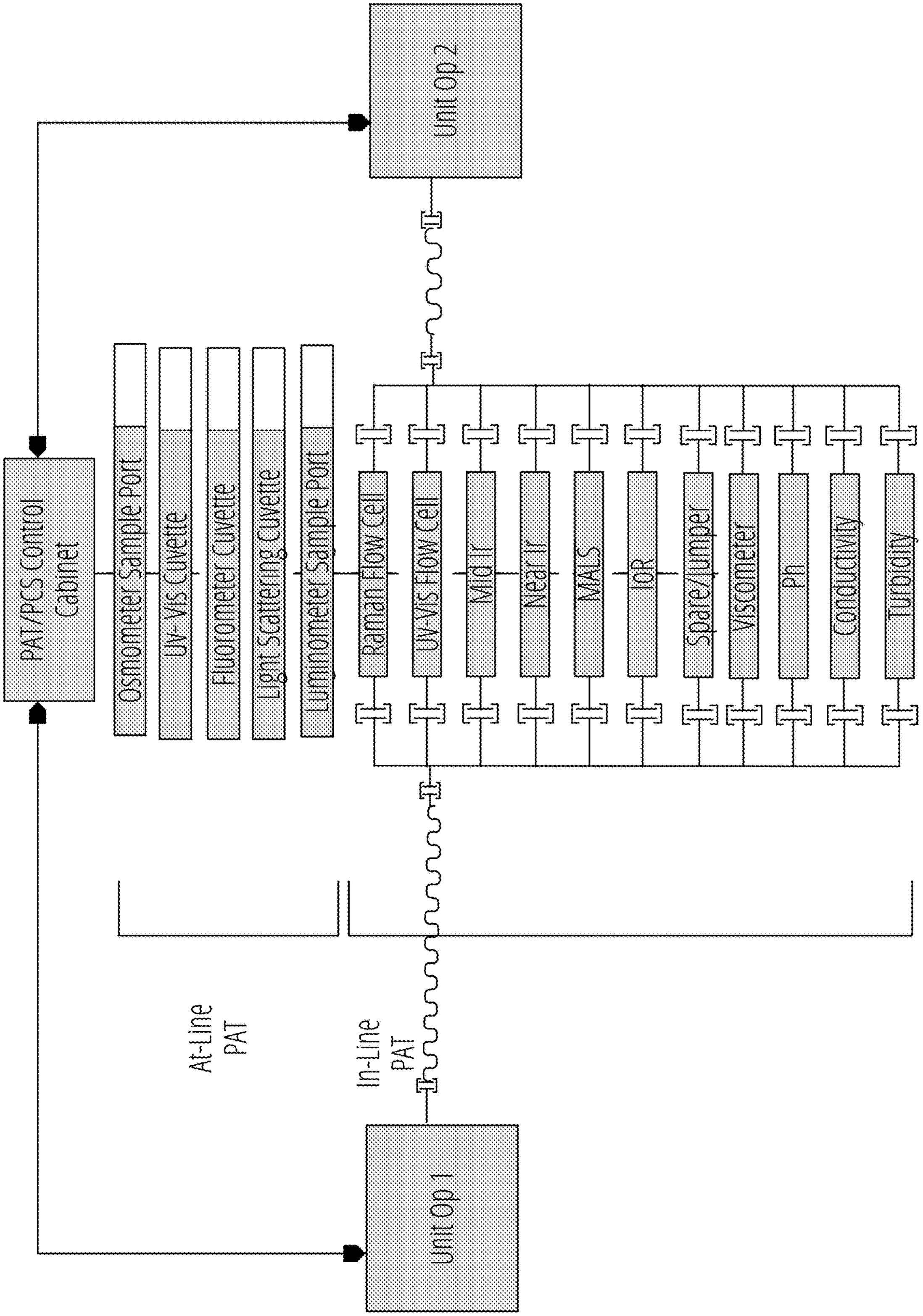
FIG. 9 is a schematic illustration in accordance with one embodiment showing examples of flow cells for in-line process analytic instruments and sample ports and cuvettes for at-line instruments.

FIG. 9 is a schematic illustrating an aspect of a PAT Box Apparatus wherein the PAT instrument stack is adapted for both at-line and in-line process analytic instruments. As shown, the PAT instrument stack includes sample ports and/or cuvettes adapted for at-line analysis, as well as flow cells for in-line analysis. Exemplary at-line PAT instruments may include an osmometer, a UV-VIS spectrophotometer, a fluorometer, a light scattering instrument, and a luminometer. In operation, an automated system or operator may obtain a sample from a unit operation or vessel and transfer it to the cuvette and/or sample port of the at-line PAT instrument for rapid analysis on the manufacturing floor.

Figure 10A:
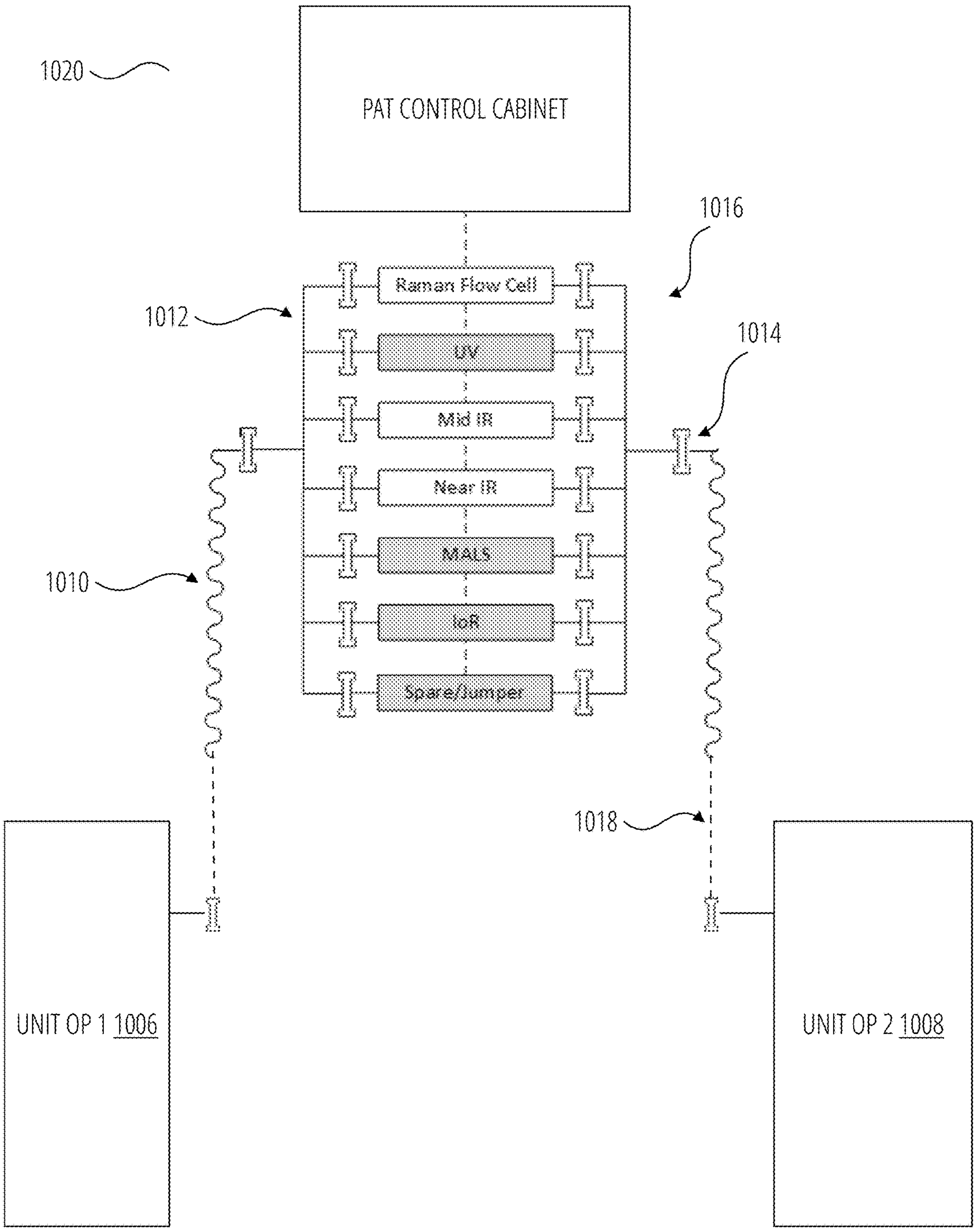
FIG. 10A is a schematic in accordance with one embodiment showing a PAT Box apparatus connected in-line between two unit operations for monitoring a continuous process. As pictured, the flow cells are integrated in parallel in the connection path.

FIG. 10A is a schematic illustrating an embodiment of a PAT Box apparatus where the PAT Box is integrated in-line between two unit operations of a pharmaceutical or biopharmaceutical manufacturing process. The schematic depicts a PAT Box apparatus situated inline between a first unit operation 1006 and a second unit operation 1008. By way of example the first unit operation may be a bioreactor unit, e.g., for culturing cells or performing an in vitro transcription (IVT) reaction, and the second unit operation may be a single pass TFF unit. Throughout this disclosure, exemplary unit operations are depicted for purposes of illustration only and are not intended to be limiting.

As illustrated in FIG. 10A, the PAT instrument stack comprises six flow cells and a spare in a parallel configuration. The PAT instrument stack is fluidly connected to the unit operations, for example, via a connector 1014 and flexible tubing 1010, as discussed above in relation to FIG. 8. The PAT Box apparatus may also include a pump for recirculating process fluid from a first unit operation through the flow cells of the PAT instrument stack and to the second unit operation, or optionally to an external vessel, or to a recycle line back to an upstream unit operation, as discussed in more detail below.

In aspects, this configuration may also include an optional vessel (not shown) external to the PAT Box apparatus housing. In aspects, the optional vessel is included in-line between a unit operation and the associated PAT Box. In aspects, the vessel is a hold vessel, a release tank, a mixing tank, a dilution tank, or a stirred tank reactor (STR). The vessel may include a plurality of ports, including IO ports for data transfer between the vessel and the PAT Box. In aspects, the vessel incorporates one or more analytical detectors, sensors and/or probes which may include one or more of an index of refraction (IoR) sensor, a conductivity sensor, a temperature sensor, pH probe, pressure sensor, turbidity sensor, oxidation-reduction potential sensor, dissolved oxygen probe, ozone sensor probe, an on-line photometer to measure silica and phosphate, a microfluidic capillary electrophoresis analyzer to measure chloride and sulfate, and/or a probe sensor to measure nitrate.

In aspects where an external vessel is not included, the configuration may also include one or more sensors, e.g., IoR sensors or other sensors, or one or more analytical detectors and/or probes at one or more of the unit operations.

In accordance with any of the foregoing aspects, the one or more analytical detectors, sensors and/or probes may include a pH sensor, conductivity sensor, temperature sensor, pressure sensor, turbidity sensor, oxidation-reduction potential sensor, dissolved oxygen probe, an ozone sensor probe, an on-line photometer e.g., to measure silica and phosphate, a microfluidic capillary electrophoresis analyzer, e.g., to measure chloride and sulfate, and a probe sensor to measure nitrate. Exemplary sensors may be depicted for purposes of illustration in various figures of the present disclosure and such exemplary illustrations are not intended to be limiting.

In aspects, this configuration may also include valves and pumps are configured to control the flow of process fluid between each unit operation and the PAT instrument stack. Operation of one or more valves and/or pumps may be controlled by a controller of the PAT Control Cabinet.

Figure 10B:
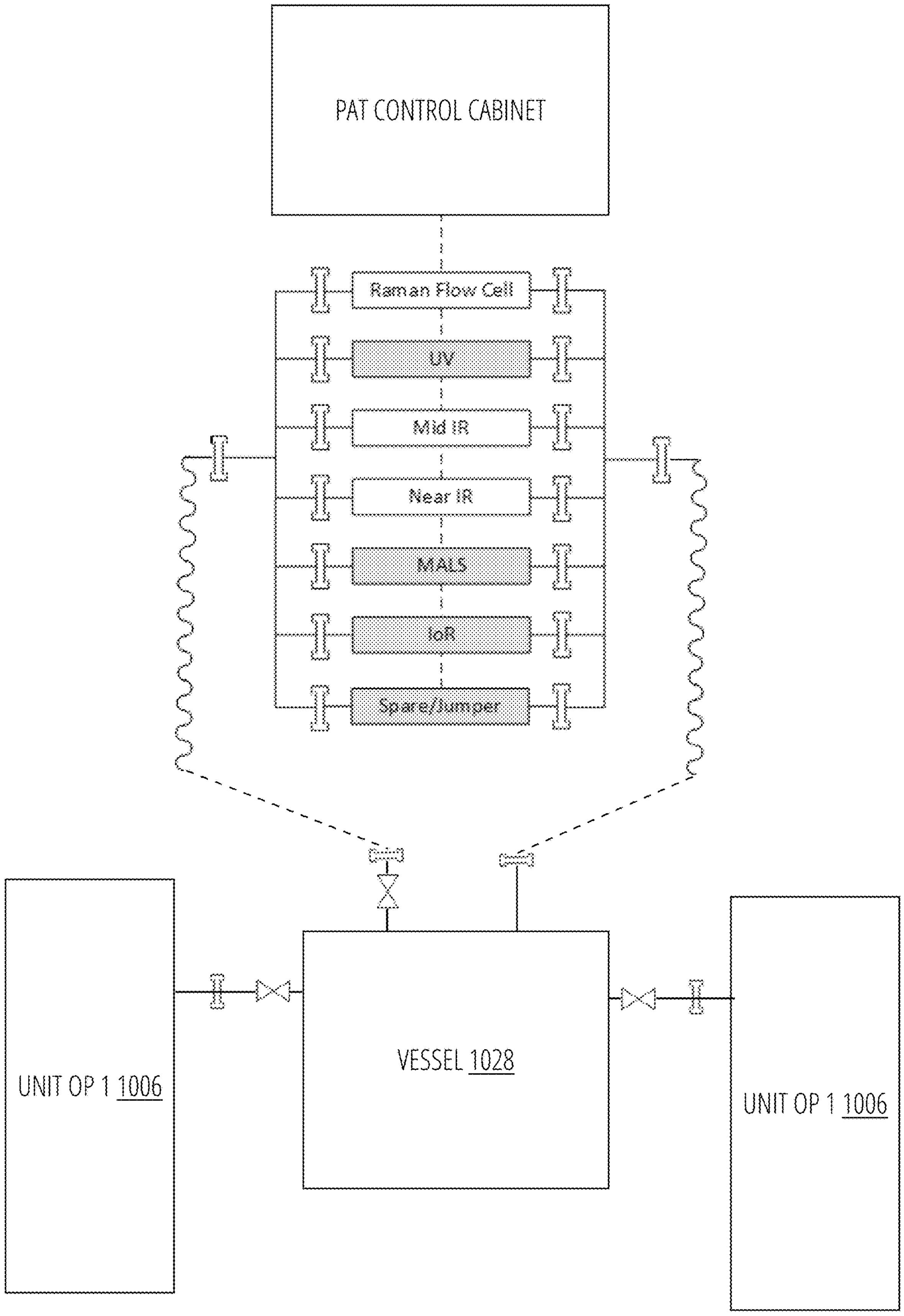
FIG. 10B is a schematic illustration of a PAT Box apparatus in accordance with one embodiment, showing the PAT Box connected to a single unit operation in a recirculation flow path where the flow cells are integrated in parallel.

FIG. 10B is a schematic illustrating an embodiment where a PAT Box apparatus is connected via a vessel 1028 situated between two unit operations of a pharmaceutical or biopharmaceutical manufacturing process. The vessel is external to the PAT Box apparatus housing and may be a hold vessel, a release tank, a dilution tank, etc. The vessel may include a plurality of ports, including IO ports for data transfer between the vessel and the PAT Box apparatus. In aspects, the vessel incorporates one or more analytical detectors, sensors and/or probes including for example, a conductivity sensor, a temperature sensor, and/or pH probe (not shown). Such probes may be connected integrally into the vessel.

Also illustrated is the PAT instrument stack where the flow cells are integrated in parallel in the flow path, as discussed above in relation to FIG. 10A. In operation, process fluid moves in a recirculation scheme from the vessel through the instrument stack and back into the vessel via operation of a pump (not shown). Fluid flow may be controlled via the coordinated operation of one or more pumps and valves. For example, suitable valves and pumps may be configured to control the flow of process fluid between (i) the upstream or first unit operation and the vessel; (ii) the vessel and the flow cells of the PAT instrument stack; and (iii) the vessel and the downstream or second unit operation. This configuration may be useful, for example, for real time release testing between unit operations in a continuous process.

Alternatively, the PAT Box may be connected to a single unit operation. An example of this use case is a unit operation that involves a biological reaction such as IVT where it would be advantageous to monitor the reaction kinetics for characterization and optimization.

Figure 11:
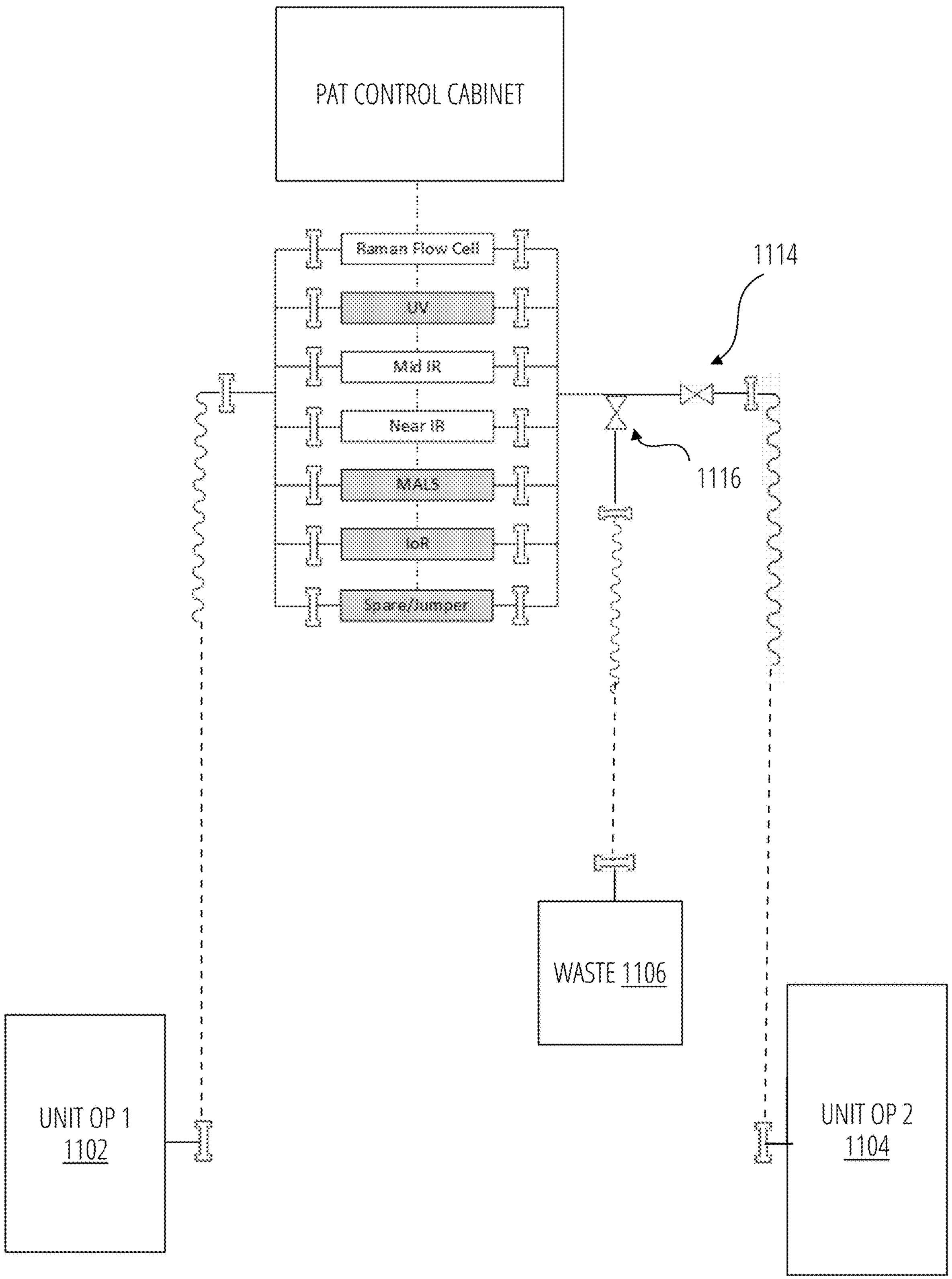
FIG. 11 is a schematic illustration of a PAT Box apparatus showing the PAT Box connected in-line between two unit operations for monitoring a continuous process, as in FIG. 10A, with the addition of a waste valve and a forward processing valve.

FIG. 11 is a schematic illustrating an embodiment of a PAT Box apparatus where the PAT Box is integrated in-line between two unit operations as depicted in FIG. 10A above, but with the addition of two smart valves, a waste valve and a forward processing valve. In this context, a "smart valve" refers to a valve that can be remotely and automatically configured to an open or closed state when certain process or analytical conditions are met by actuation of control software. Such smart valves are commercially available, for example, one option for a "smart" valve is a pneumatically operated diaphragm valve manufactured by GEMU, or the GEMU electrically operated single use pinch valve. In operation, the forward processing valve remains closed when in-process testing criteria measured by the PAT flow cells is not met. Where the criteria are satisfied, the forward processing valve opens and process fluid is allowed to flow to the next unit operation (Unit Operation 2). The waste valve may be opened or remains open when in-process testing criteria measured by the PAT flow cells is not met. Where the criteria are satisfied, the waste valve closes.

Figure 12A:
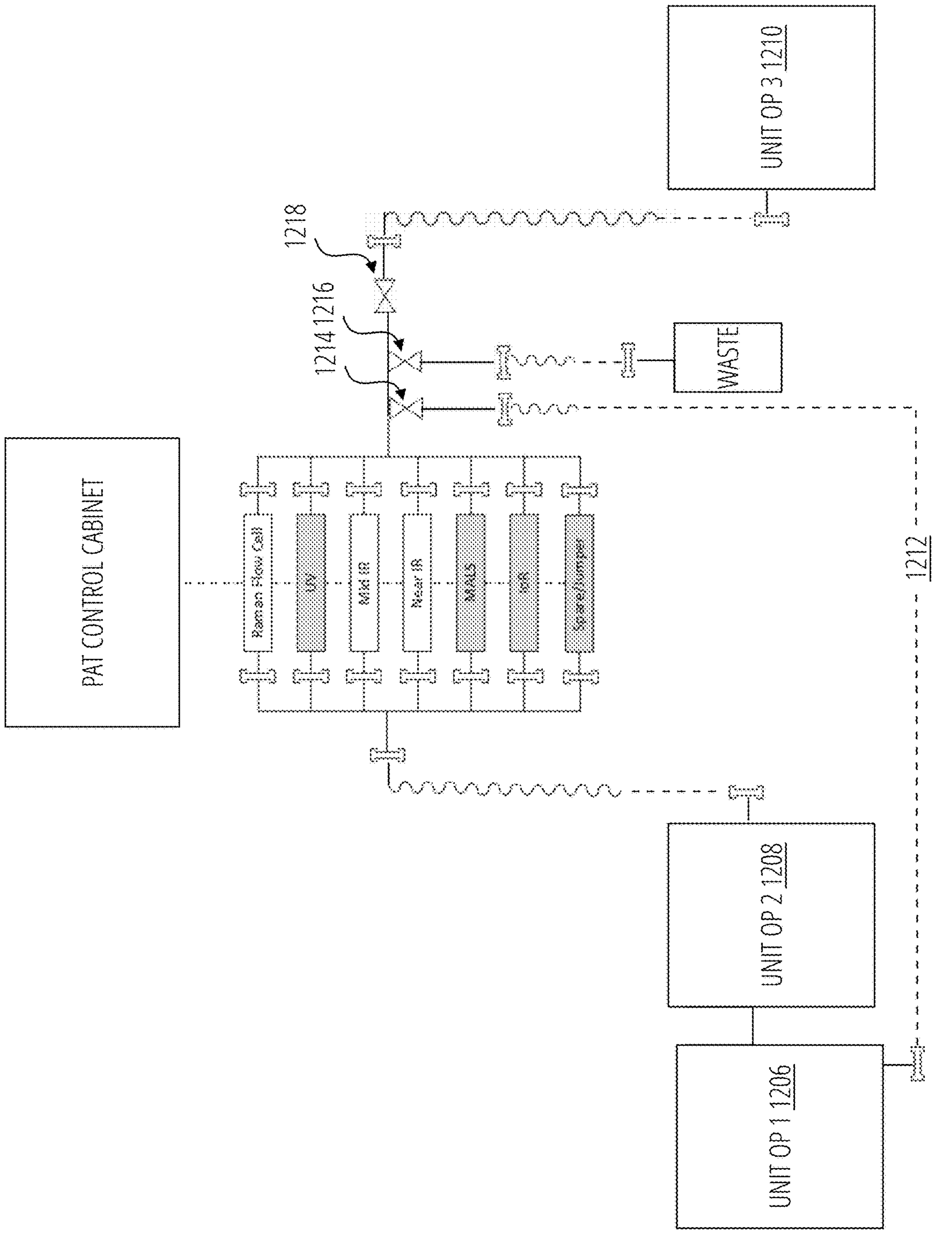
FIG. 12A is a schematic illustration of a PAT Box apparatus showing a configuration for real time release testing between two unit operations in a continuous process with a waste collection vessel, waste valve, forward processing valve and reagent return/material recycling valve.

FIG. 12A is a schematic illustrating a configuration where the PAT Box is integrated in-line between two unit operations of a manufacturing process, depicted as 1208 and 1210. This configuration may be used, for example, for real time release testing at Unit Op 2 1208. In operation, process fluid from a first unit operation 1206, for example a bioreactor or IVT reaction vessel, flows to a second unit operation 1208 and then passes into the flow cells of the PAT instrument stack, depicted here in a parallel configuration with respect to the flow path. Three smart valves are positioned downstream of the instrument stack, each operating to open or close a fluid conduit connected to a unit operation for recycling 1214, a waste container 1216, or the next unit operation in the manufacturing process 618. As illustrated, the material recycle valve 1214 controls access to a reagent recovery loop 1212 in fluid communication with the first unit operation 1206. This configuration may be used, for example, to recover and/or recycle reagents back to the first unit operation. The waste valve 1216 controls access to a waste conduit in fluid communication with a waste vessel. The forward processing valve 1218 controls access to a conduit in fluid communication with the downstream unit of operation 1210. In operation, each of the smart valves is actuated in accordance with predetermined in-process criteria as measured by the PAT flow cells.

Figure 12B:
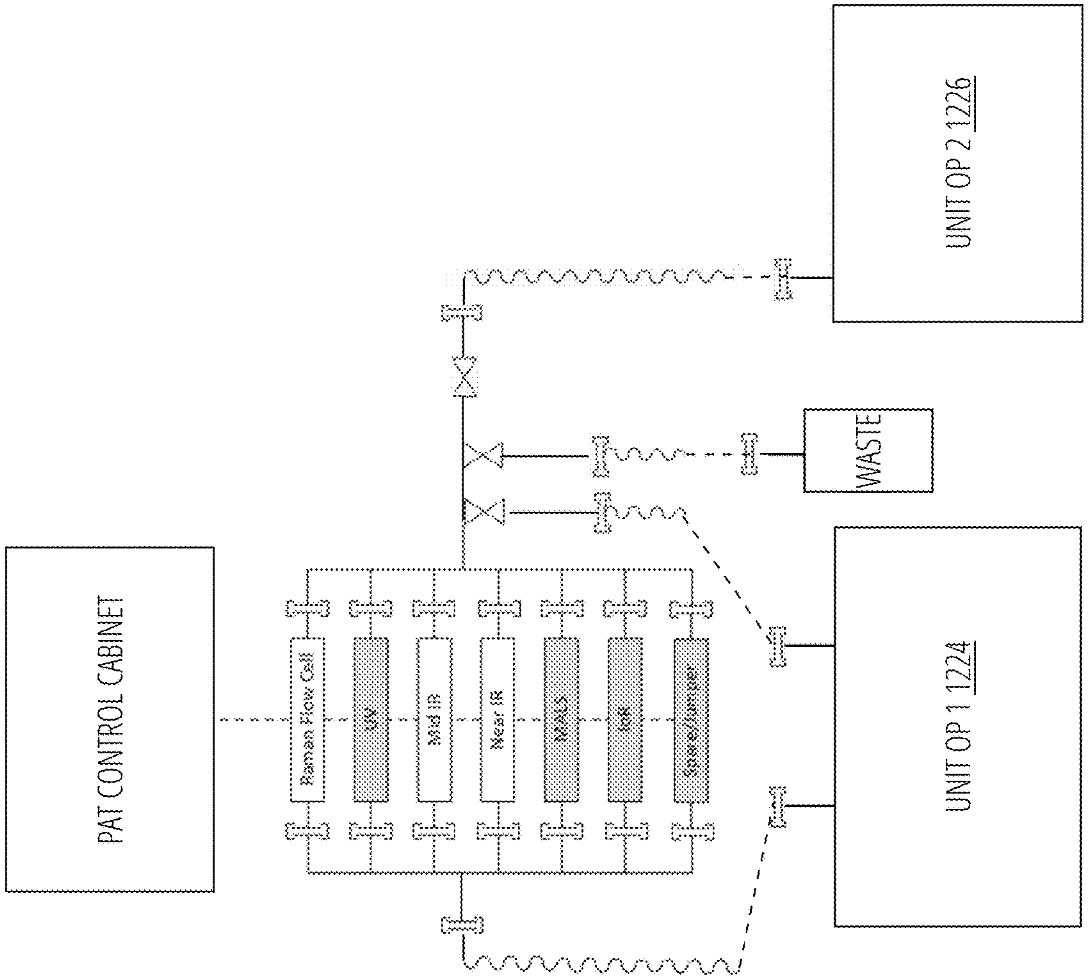
FIG. 12B is a schematic illustration of a PAT Box apparatus showing another configuration for real time release testing where the apparatus is positioned at a first unit operation in the continuous process with a waste collection vessel, waste valve, forward processing valve and reagent return/material recycling valve.

FIG. 12B illustrates a configuration where the PAT Box is integrated at a first unit operation, Unit Op 2 1208. In operation, process fluid recirculates through the instrument flow cells and may be recycled back into the unit 1224 via the recycle valve. Where process criteria are met, the recycle valve closes, the waste valve remains closed, and the forward processing valve is opened, allowing the process material to pass to the next unit operation, 1226. If the criteria are not met or deemed to be sub-standard, the waste valve may be opened to send process fluid to a waste container.

To further illustrate this configuration by way of an example, the first unit operation may be a single pass TFF and the process fluid may be recycled through the TFF until a predetermined concentration condition is met. At the point, the process fluid would be allowed to pass to the next unit operation. Otherwise, the process material could be allowed to go to waste.

Figure 13:
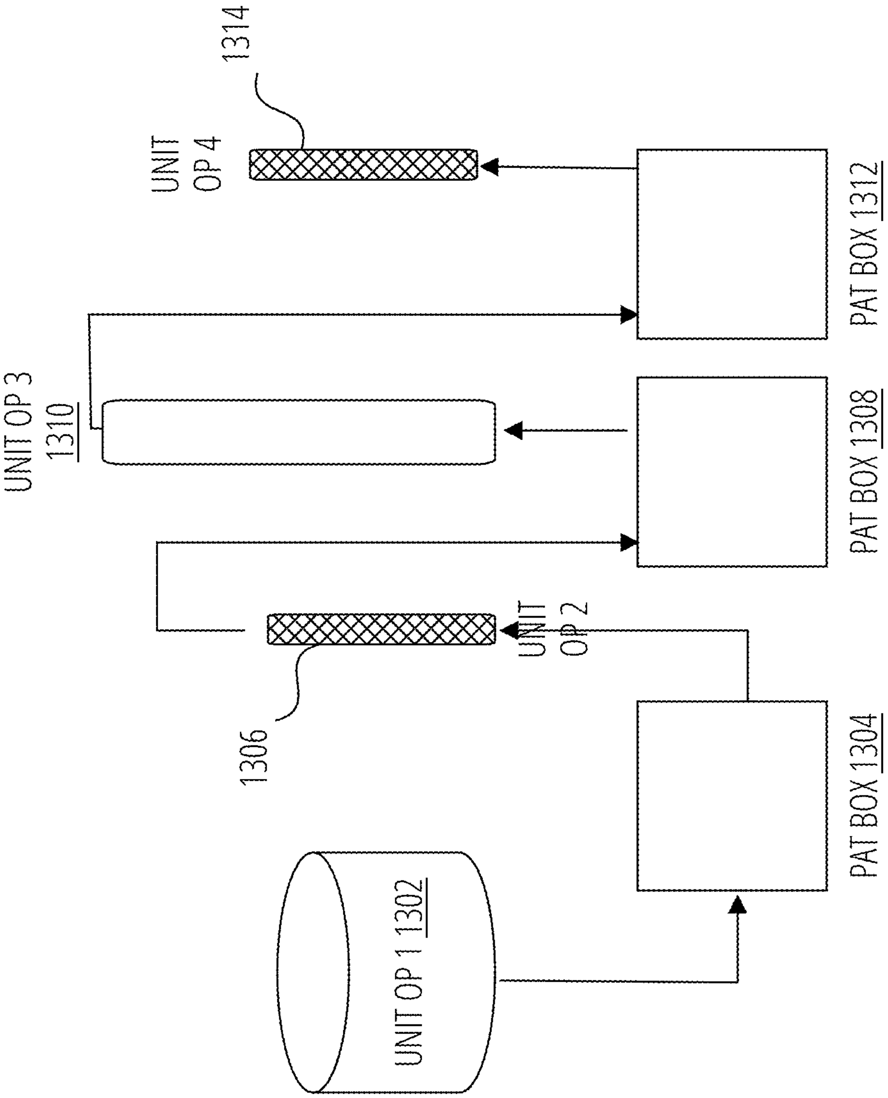
FIG. 13 is a schematic illustrating an exemplary biopharmaceutical manufacturing system in accordance with one embodiment, showing several PAT Box apparatuses connected in-line between unit operations for monitoring a continuous process.

FIG. 13 is a schematic illustrating a configuration where a plurality of PAT Box apparatuses are integrated inline between subsequent unit operations of a pharmaceutical or biopharmaceutical manufacturing process. The schematic depicts a system including a first inline PAT Box 1304 situated inline between a first unit operation 1302, which may be, for example, a bioreactor or IVT reaction vessel, and a second unit operation 1306, which may be, for example, a tangential flow filtration (TFF) module. A second PAT Box 1308 is situated inline between the second unit operation 1306 and a third unit operation 1310, which may be, for example, a chromatography module. A third PAT Box 1312 is situated inline between the third unit operation 1310 and a forth unit operation 1314, which may be, for example, a second TFF module. In operation, each PAT Box is configured with a set of flow cells and instruments to measure process parameters including CPPs and/or CQAs, compare the measured parameters against predetermined criteria, and control the flow of process fluid from one unit operation to the next, for example via control of smart valves as discussed above. Accordingly, this configuration may also include valves and pumps configured to control the flow of process fluid between each unit operation and the PAT Box, as detailed above in relation to FIG. 12A and FIG. 12B.

The versatility of the PAT Box apparatus is such that it may be adapted for monitoring and control of diverse unit operations, including a biological reaction operation, such as IVT, a filtration operation, a chromatography operation, a lipid nanoparticle (LNP) multi-phase mixing operation, and/or an excipient addition operation. Other unit operations may include a fermentation operation, a cell lysis operation, a protein capture operation, a viral inactivation/filtration (VI) operation, an enzymatic reaction operation, a fill/finish operation, and/or a polishing operation.

Figure 14:
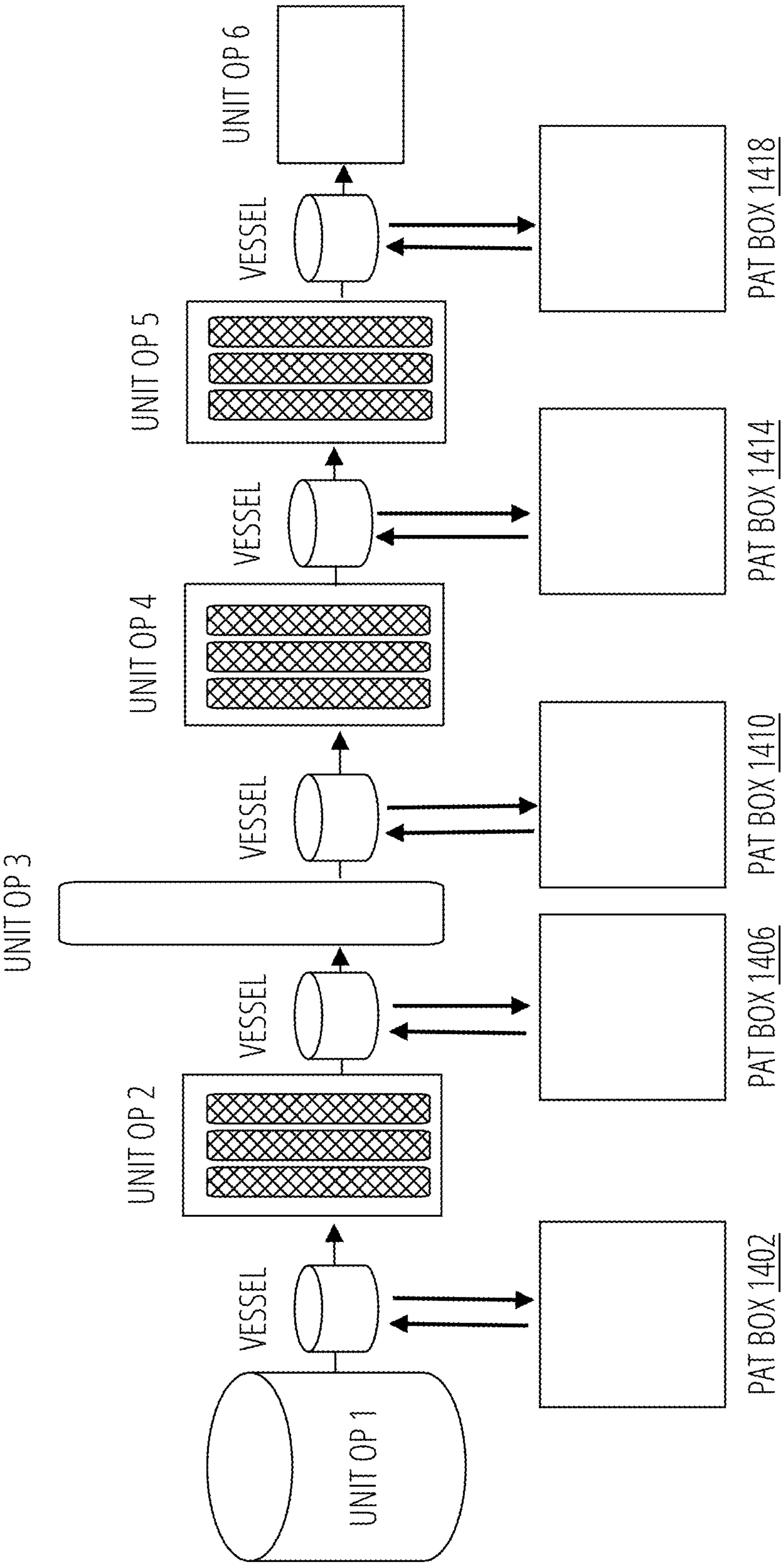
FIG. 14 is a schematic illustrating an exemplary biopharmaceutical manufacturing system in accordance with one embodiment where several PAT Box apparatuses are connected between unit operations via a vessel, such as a surge vessel.

FIG. 14 is a schematic illustrating a configuration where several PAT Box apparatuses are integrated into a manufacturing process as in FIG. 13, but instead of being directly connected between each unit operation, the PAT Box apparatuses are each connected via an external vessel to a unit operation in the process. The vessels may be situated in-line between one or more of the unit operations and the associated PAT Box. In aspects, the vessel is a hold vessel, a release tank, a dilution tank, or a stirred tank reactor. The vessel may include a plurality of ports, including IO ports for data transfer between the vessel and the PAT Box. In aspects, the vessel incorporates one or more analytical detectors, sensors and/or probes including for example, a conductivity sensor, a temperature sensor, and/or pH probe.

In operation, a first PAT Box 1402 monitors and optionally controls a process within a first unit operation (Unit Op 1). A second PAT Box 1406 monitors and optionally controls a second unit operation (Unit Op 2). Subsequent PAT Boxes, 1410, 1414, and 1418 monitor and optionally control other downstream units of operation. In aspects, this configuration may also include valves, including smart valves, and pumps configured to control the flow of process fluid between each unit operation, the external vessel and the PAT Box. The PAT Box apparatuses are configured for easy integration at key points in the manufacturing process, for example via the use of standard connectors such as tri-clamps, quick connects, etc., to connect the vessels to the unit operations and to the PAT Boxes.

This configuration may be useful, for example, during process development to identify CCPs for monitoring and control. This configuration may also be useful for real time release and/or verifying in-process control measurements are within limit criteria for forward processing.

In aspects, the flow path may be configured such that the process fluid from a given unit operation recirculates through the flow cells of the in-line PAT Box and returns to the same unit operation, for example as illustrated in connection with FIG. 12B. Alternatively or in addition, the flow path may contain one or more "smart" valves configured to control the flow of process fluid back to a unit operation for recycling, or to a waste container, or forward to the next unit operation in the manufacturing process, depending on whether or not predetermined criteria are satisfied, for example as illustrated in FIG. 12A and FIG. 12B.

Figure 15:
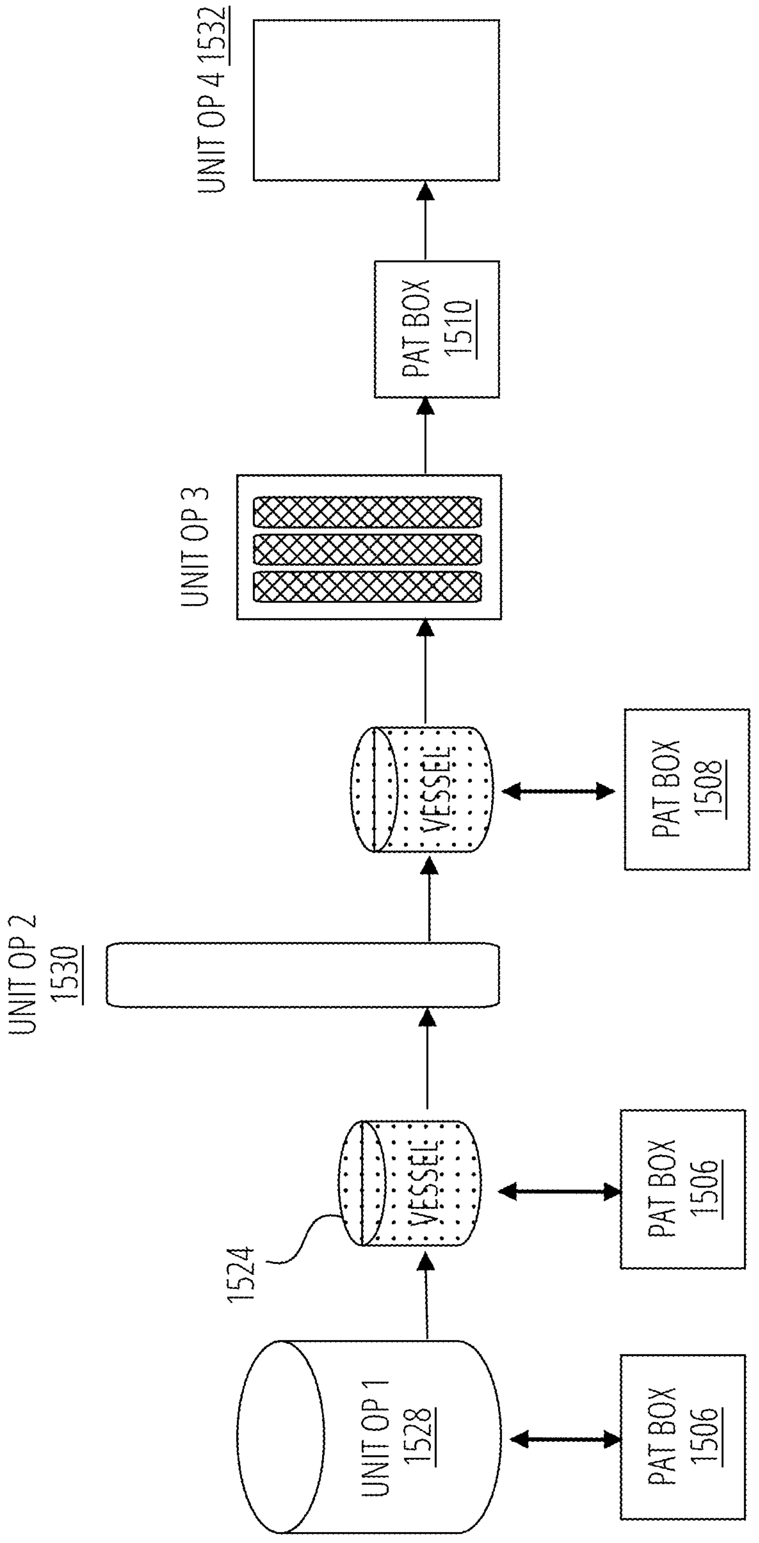
FIG. 15 is a schematic illustrating an exemplary biopharmaceutical manufacturing system in accordance with one embodiment where several PAT Box apparatuses are connected between unit operations via a vessel, such as a surge vessel and another PAT Box apparatus is situated in-line between unit operations.

FIG. 15 is a schematic illustrating a configuration of a manufacturing process where a plurality of PAT Box apparatuses are integrated in different ways. As depicted here, the manufacturing process may be made continuous or integrated with surge or hold vessels configured between the unit operations. PAT Boxes may be integrated and connected to these vessels to monitor and control the process. PAT Boxes may also be placed in-line between unit operations or integrated directly into a unit operation, for example to monitor an IVT reaction, a cell culture, or fermentation. With reference to FIG. 15, a first PAT Box 1506 is configured to recirculate process fluid from a first unit operation 1428 and return the process fluid to the same unit operation. The next two PAT Boxes 1506 and 1508 are configured to connect to an external vessel 1524 which is in-line between two unit operations in the process. The external vessel may be a hold vessel, a release tank, a dilution tank, or a stirred tank reactor and may include one or more of an IO port for data transfer and one or more analytical detectors, sensors and/or probes, as described above in connection with FIG. 14. A third PAT Box 1510 is situated in-line between the last two unit operations in the process, for example as described above in connection with FIG. 13.

It is understood that here also the flow path may be configured such that the process fluid from a given unit operation recirculates through the flow cells of the in-line PAT Box and returns to the same unit operation, and/or the flow path may contain one or more "smart" valves configured to control the flow of process fluid back to a unit operation for recycling, or to the waste container, or forward to the next unit operation in the manufacturing process, depending on whether or not predetermined criteria are satisfied, as discussed above.

Figure 16:
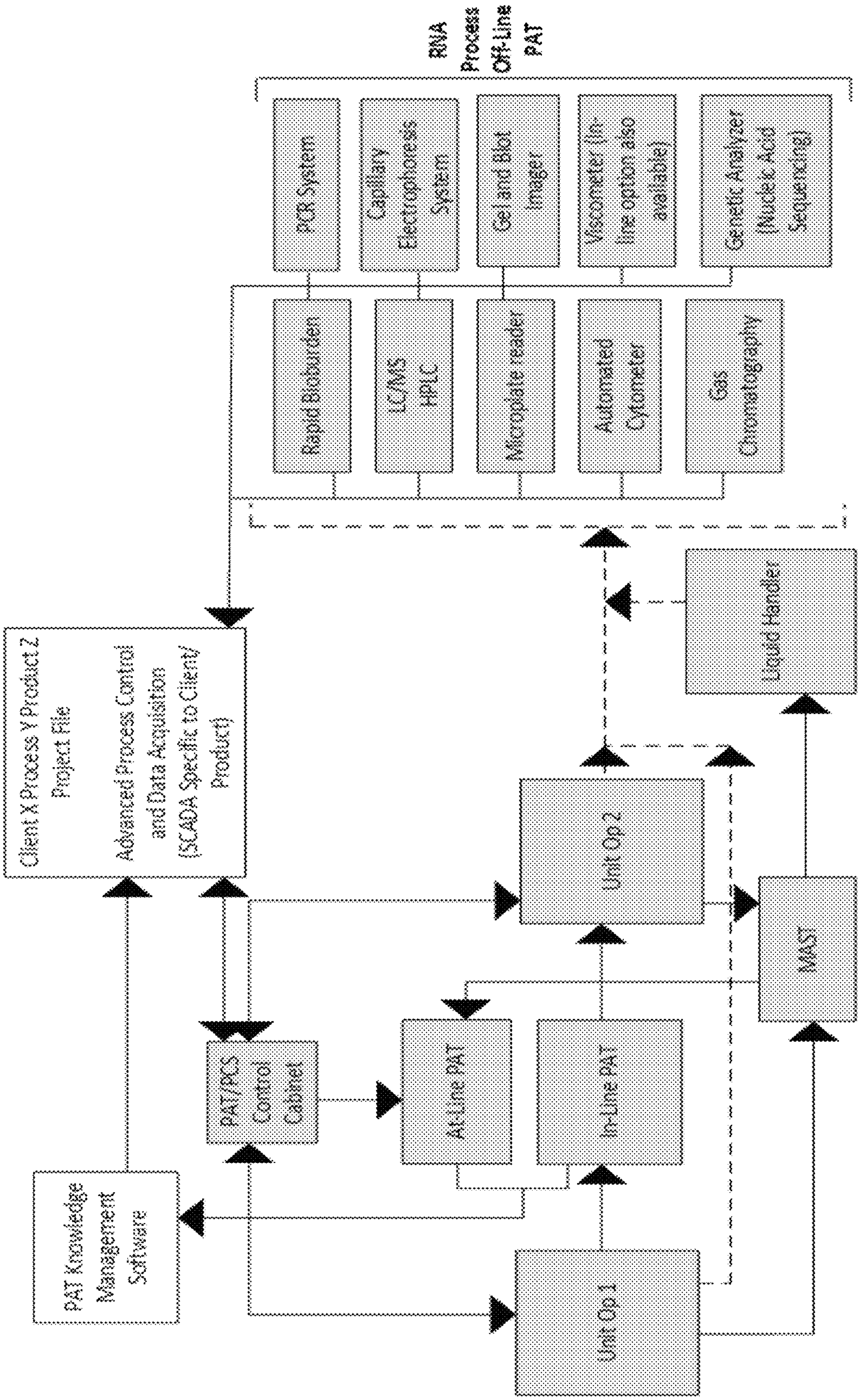
FIG. 16 is a schematic diagram illustrating the possible use by the PAT Box apparatus of in-line, at-line, and off-line process analytical data.

FIG. 16 is a schematic illustrating integration of a PAT Box apparatus including in-line and at-line analytic instruments with unit operations, off-line instruments, process specific SCADA and a project file data. In operation, the PAT Control Cabinet, e.g., via its APC and SCADA, receives data from the PAT instrument stack which is connected to the in-line and/or at-line instruments, shown for illustration purposes as situated between two unit operations of a process. The PAT Control Cabinet processes the data and may also be configured to send commands to the at-line and in-line analytic instruments via the PAT Knowledge Management software and SCADA.

Data from off-line analytic instruments may be incorporated via automatic or manual sampling and transfer (dashed line) of process fluid to the off-line instruments. Raw data from off-line analytics is transferred to a project file which is accessed by the PAT Knowledge Management software.

Illustrated are non-limiting examples of off-line process analytic instruments including a rapid bioburden instruments, LC-MS and HPLC instruments, a microplate reader, an automated flow cytometer, a gas chromatograph, a polymerase chain reaction (PCR) system, a capillary electrophoresis system, a gel and/or blot image system, a viscometer, and a nucleic acid sequencer.

A system comprising one or more PAT Box apparatuses and associated digital architecture provides a universal solution to fully integrate any pharmaceutical or biopharmaceutical manufacturing process with a wide range of process analytic tools. In this context, the term "digital architecture" refers to the design and integration of hardware, software, networks, and data structures. For example, the digital architecture includes servers that store process data, analytic data, and offline data, the software that enables interactions between the data, and the protocols that govern how data is shared between system components. In aspects, the digital infrastructure may include a Knowledge Hub which may include process specific data, including historical process run and analytical data, design of experiments (DOE) and process development and design space data, as well as clinical data. In aspects, user data may be fed into the Knowledge Hub by any one or more of import algorithms on csv and/or propriety data, manual entry, online portal and form, and/or LIMS facilitates sample integrity from off-line instruments and data transfer to Knowledge Hub.

Accordingly, in an aspect provided is a PAT Box apparatus configured to connect and send information to a Knowledge Hub, e.g., via PAT Knowledge Management software. In accordance with this aspects, the PAT Box apparatus may be configured to transmit data including spectrogram, chromatogram, and particle size density that may include over 3000+ points per second averaged over a specified period of time. In aspects, the data is converted into useful process parameters including e.g., concentration, particle size, purity, etc., for example by appropriate models. In aspects, the models may interface with a digital twin to model critical quality parameters and critical process parameters. The digital twin models may include mechanistic, data-driven, machine learning, and hybrid models that incorporate different physics and phenomena in the process. The digital twin may also interface with machine learning and optimization algorithms that optimize the process for performance, cost, and yield. The Knowledge Hub may also transmit adjustments or process recipes directly to the control system, e.g., by sending command bits to PAT instruments and smart valves for monitoring, open/close etc. Human operators at the control system may acknowledge or dismiss based on the floor priorities. The control system may also runs through system checks to acknowledge new parameters are within a control range.

A prototype PAT Box Apparatus was constructed which included the following instruments:

1. Raman Instrument (MarqMetrix AIO)
2. UV VIS Instrument (Repligen CTech FlowVPX)
3. Mid-IR Instrument (IRUBIS)
4. NIR Instrument (Avantes)
5. Multi Angle Light Scattering (MALS) Instrument (Waters)
6. DLS Instrument (nanoparticle size analyzer, INPROCESS NanoFlowSizer)

The instruments where housed on a custom skid which also include power, communications, and pump components. Data was collected to train models for prediction of CQAs in mRNA drug substance (DS) and drug product (DP) unit operations. The following Figures and associated descriptions highlight the functions of the PAT Box Apparatus operation in practice.

Figure 17:
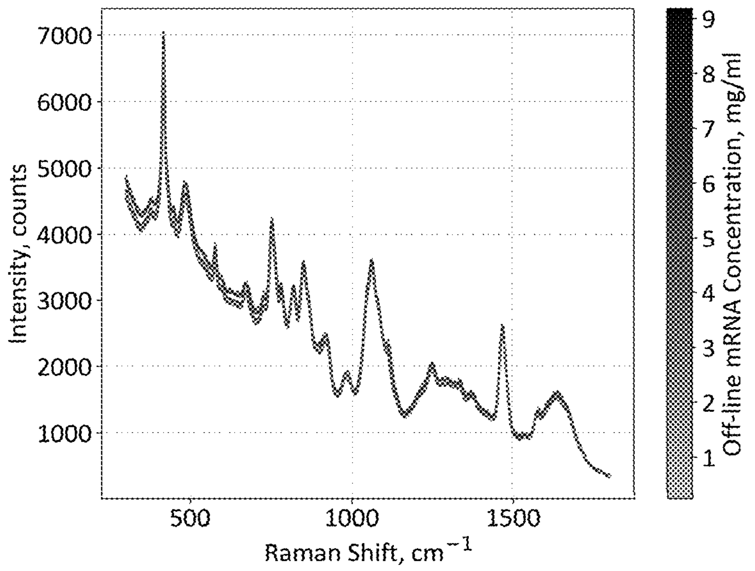
FIG. 17 is a graph illustrating raw spectra collected from an in-line Raman flow cell showing Raman shift in $cm^{-1}$ on the x-axis and intensity in counts on the y-axis.
Figure 18:
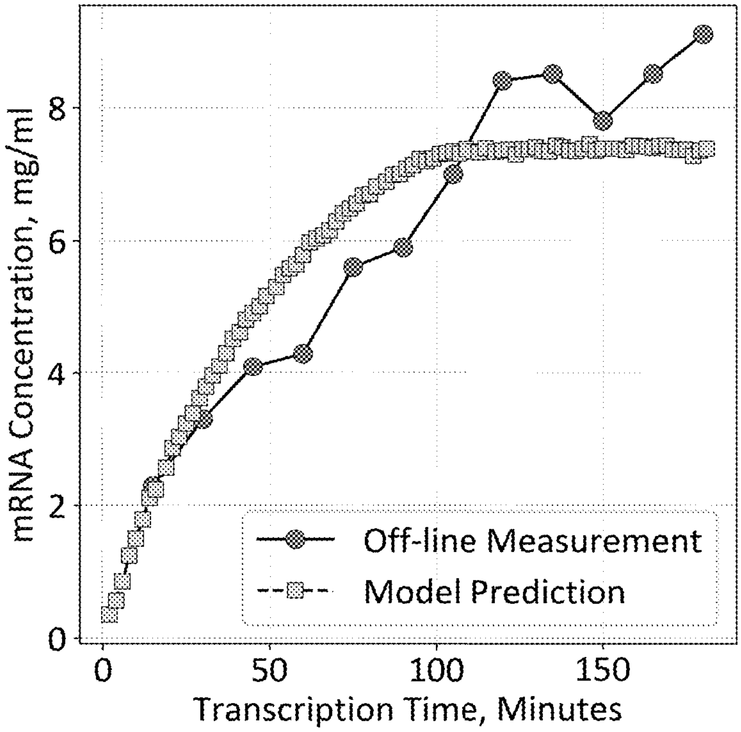
FIG. 18 is a graph of mRNA concentration versus time illustrating PLS model predictions (squares) compared to off-line UV-VIS measurements (circles) for the IVT test operation.

Example 1—Using Raman to Measure mRNA and NTP Concentration at IVT Unit Operations A PLS model was trained using in-line Raman data collected during multiple IVT runs and calibrated using off-line UV-VIS measurements. This model was then used to predict mRNA concentration during additional IVT runs by feeding Raman data to the model in real-time. The Raman instrument collected one measurement per two minutes. The data was fed into the PLS model in real-time and model predictions were generated in real-time. Additional off-line samples were collected during the run to compare with the model predictions. FIG. 17 is a graph illustrating raw spectra collected from an in-line Raman flow cell collected during an IVT test operation. The PLS model predictions for mRNA concentration over time are shown in FIG. 18 as compared to off-line UV-VIS measurements for the IVT test operation.

Figure 19:
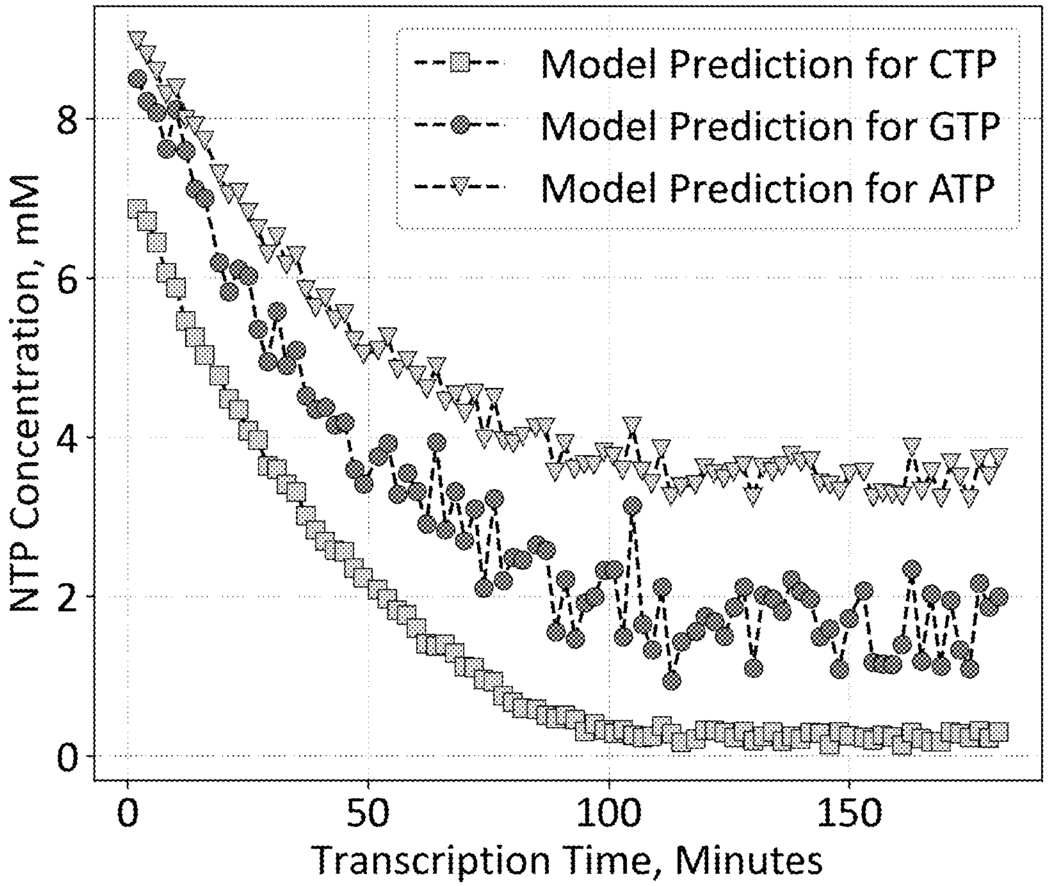
FIG. 19 is a graph illustrating PLS model predictions for the IVT test operation.

FIG. 19 is a graph showing PLS model predictions of NTP concentration (mM) versus transcription time (min) for the IVT test operation based on Raman spectroscopy measurements. Predicted CTP, GTP, and ATP concentrations are shown by squares, circles and triangles, respectively.

The use of in-line Raman technology for measuring critical quality attributes (CQA's) such as NTP concentration as illustrated in this example represents an improved method for several reasons. For example, as an in-line analytic, it obviates the need for manual sampling and allows for real-time data acquisition. The models developed are also used in real-time to monitor the process CQAs thereby providing instantaneous information about process performance. In-line Raman technology as described herein represents an alternative to off-line analytical methods such as UV or HPLC which may take hours to obtain the information required to move a process forward to the next step of the production. During off-line testing a process cannot move forward until results are verified, presenting a bottleneck in analytics and process holding step(s). There is also lack of real-time acquisition in manual operation as samples are taken out by an operator rather than automated and measured via technology in place, such as Raman.

This example demonstrates in-line Raman flow cell measurement of an in vitro transcription unit operation. The flow cell measurement enabled implementation of Raman measurement to various scales from 10 ml-250 ml bioreactors, making this technology scale agonistic. In order to adapt Raman analytics to in-line continuous measurement, it was necessary to overcome engineering challenges such as maintaining the process temperature. This was accomplished using insulation and a shorter re-circulation tube combined with increasing the flow rate in the re-circulation loop. At the same time, Raman acquisition parameters were optimized to achieve enough spectral quality to distinguish between fingerprint of different process components.

Figure 20:
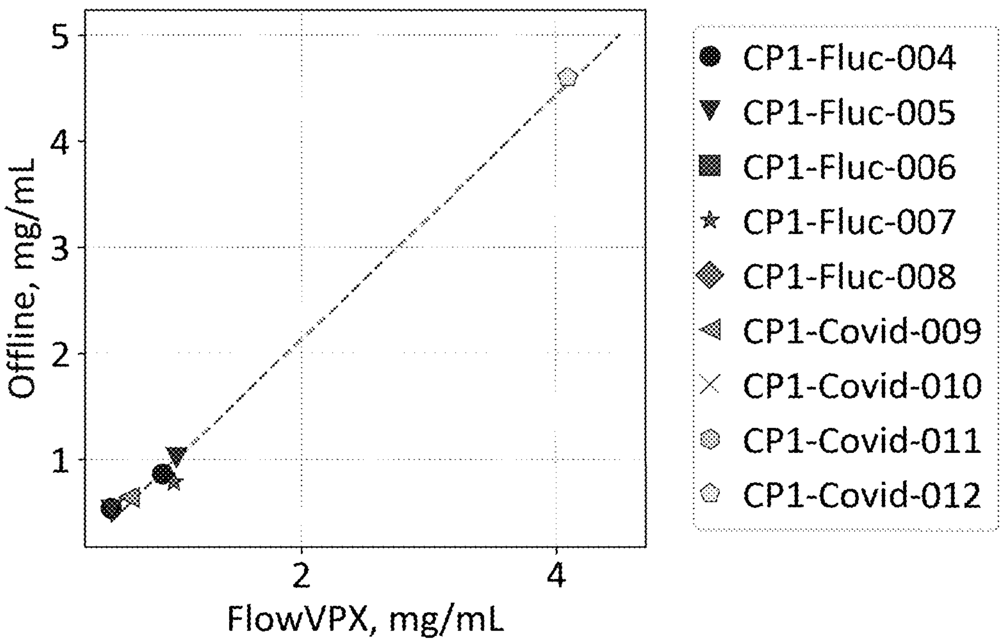
FIG. 20 illustrates a plot of in-line FlowVPX measurements vs off-line UV-VIS measurements at TFF1 pool.
Figure 21:
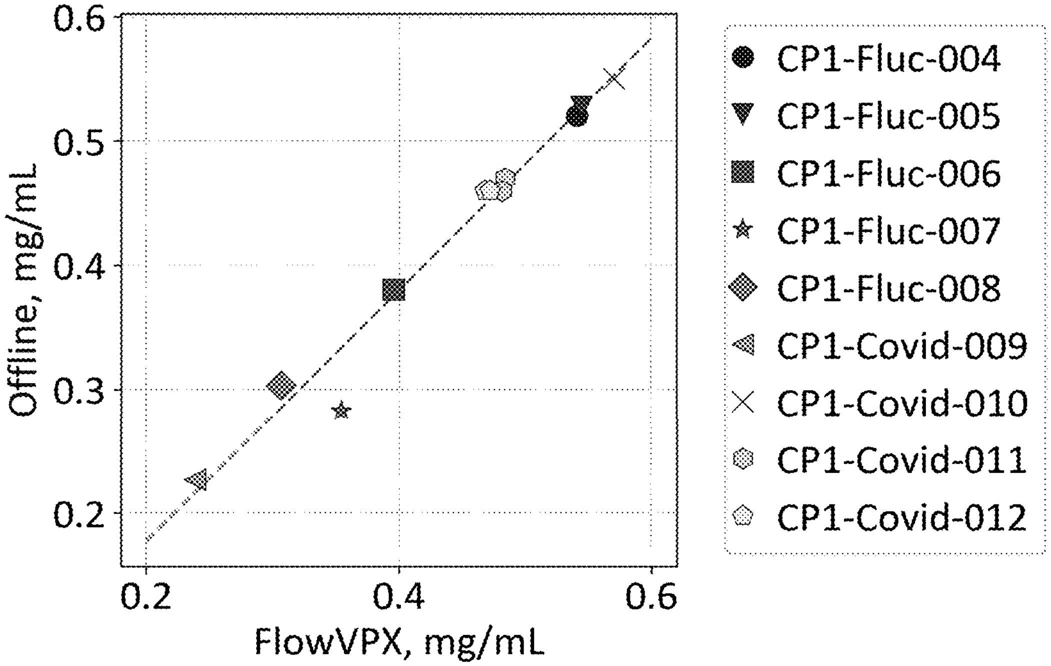
FIG. 21 illustrates a plot of in-line FlowVPX measurements vs off-line UV-VIS measurements at OdT pool.
Figure 22:
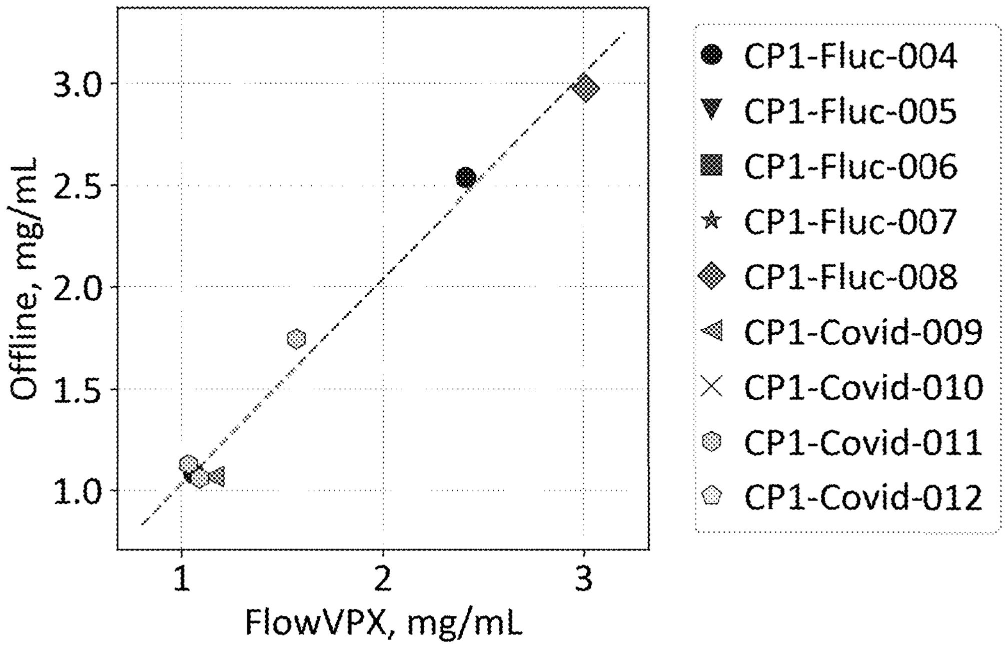
FIG. 22 illustrates a plot of in-line FlowVPX measurements vs off-line UV-VIS measurements at TFF2 pool.

Example 2—Using in-Line UV-VIS to Measure mRNA Concentration at Downstream Unit Operations In this example of a continuous process, the IVT unit operation is followed by a first tangential flow filtration (TFF1) operation, an oligo-dT affinity chromatography (OdT) operation, and a second tangential flow filtration (TFF2) operation. UV-VIS instruments were used in an in-line flow cell setup to measure mRNA concentration in real-time at three points in the continuous process, at a TFF1 pool, a OdT pool, and a TFF2 pool. The results of these measurements were compared to off-line UV-VIS measurements for validation purposes. FIG. 20 illustrates the correlation between in-line UV-VIS mRNA concentration measurements (mg/ml) and off-line UV-VIS measurements at the TFF1 pool. The $R^2$ is equal to 0.99. The RMSE is equal to 0.19 mg/mL. FIG. 21 illustrates the correlation between in-line UV-VIS mRNA concentration measurements (mg/ml) and off-line UV-VIS measurements at the OdT pool. The $R^2$ is equal to 0.97. The RMSE is equal to 0.02 mg/mL. FIG. 22 illustrates the correlation between in-line UV-VIS mRNA concentration measurements (mg/ml) and off-line UV-VIS measurements at the TFF2 pool. The $R^2$ is equal to 0.98. The RMSE is equal to 0.04 mg/mL.

These results demonstrate the feasibility of using in-line UV-VIS analytics to measure mRNA concentration during a continuous mRNA manufacturing process, avoiding the need for process holds at critical points as required for off-line analytical methods. Real-time monitoring of mRNA concentration as demonstrated here also enables data-driven decisions to support faster and more effective production of the therapeutic. These methods are also useful to predict at which point in production a problem may be occurring due to the ability to see in real time where product specifications are not being met.

Example 3—Using Mid-IR to Measure mRNA Concentration at IVT Unit Operation

Figure 23:
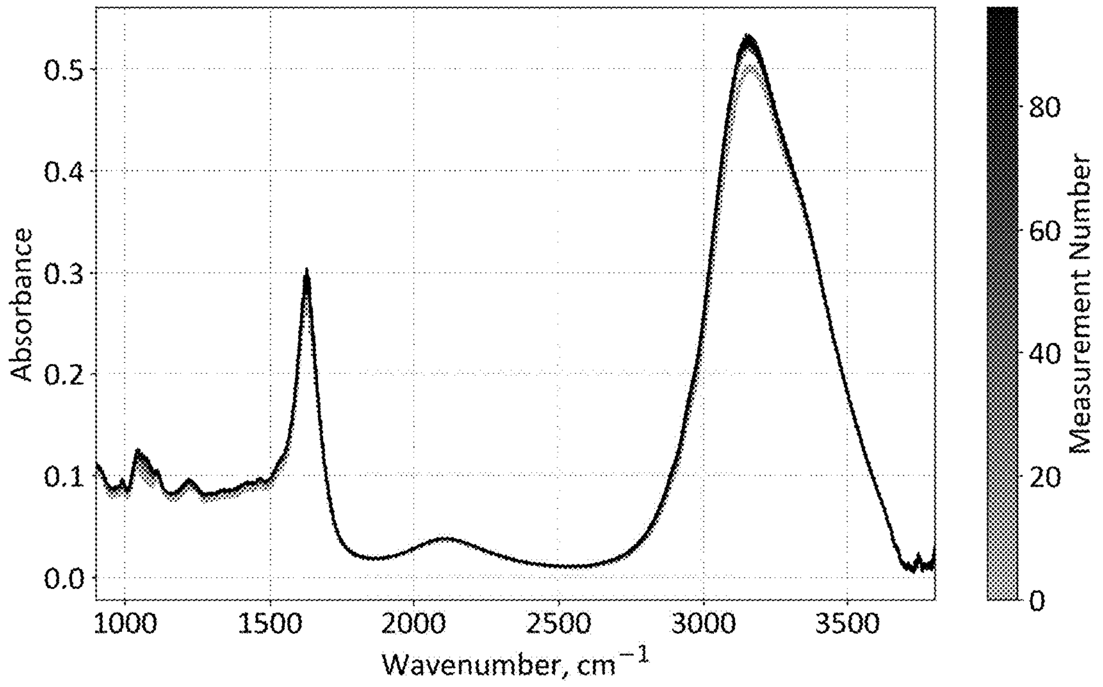
FIG. 23 illustrates raw spectra collected from in-line Mid-IR flow cell in the IVT run. The graph illustrates the Raman shift in $cm^{-1}$ on the x-axis and the absorbance on the y-axis.
Figure 24:
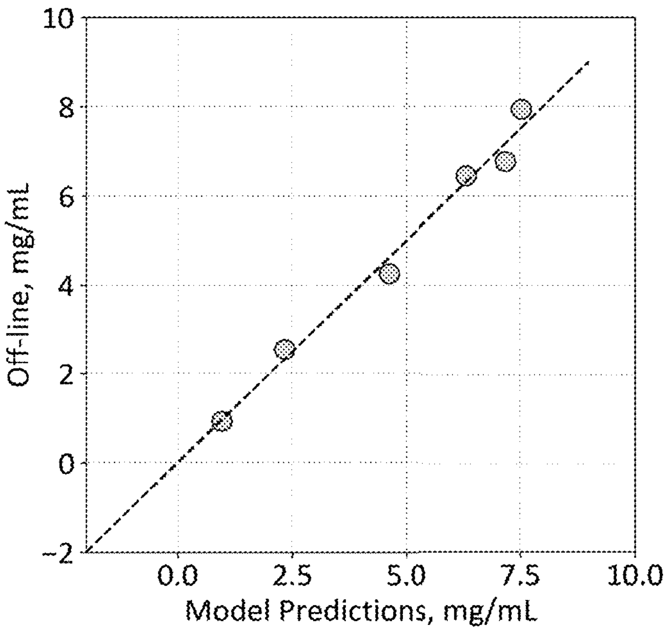
FIG. 24 illustrates a PLS model training plot showing alignment of off-line UV-VIS measurements to the PLS model predictions.
Figure 25:
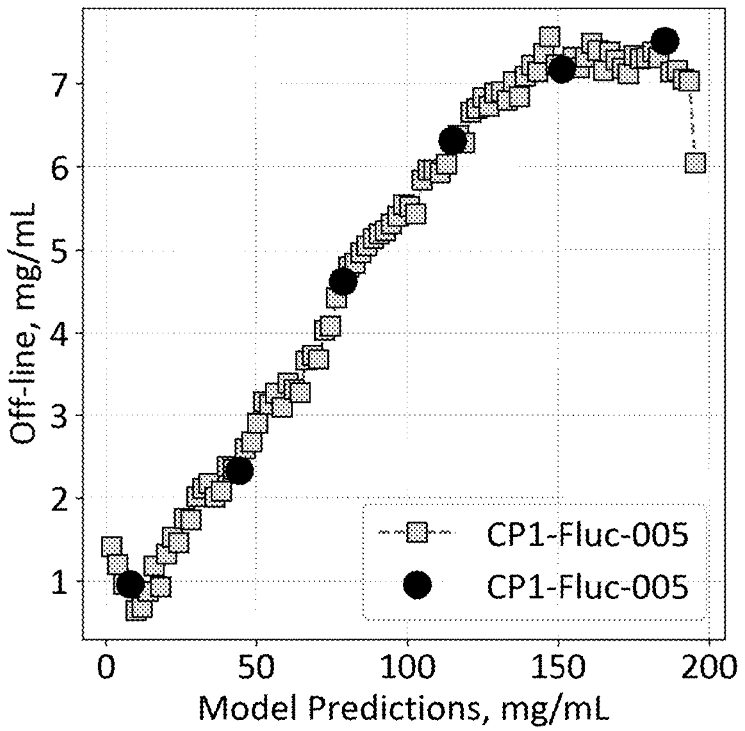
FIG. 25 illustrates a PLS model prediction of all measurements taken during CP1-Fluc-005 vs off-line UV-VIS measurements.

In this example, a PLS model was trained using in-line Mid-IR data collected during an IVT run CP1-Fluc-005 and calibrated using off-line UV-VIS measurements. FIG. 23 illustrates raw spectra collected from in-line Mid-IR flow cell in the IVT run. FIG. 24 illustrates a PLS model training plot showing alignment of off-line UV-VIS measurements to the PLS model predictions. The $R^2$ is equal to 0.99. The RMSE is equal to 0.3 mg/mL. FIG. 25 illustrates PLS model prediction (squares) of all measurements taken during the IVT run compared to off-line UV-VIS measurements (circles).

Similar to Raman and UV, midIR technology allows real-time integration of the system into a process workflow. Sample during production is measured in real-time and information is then obtained to make a decision if enough of the product or CQA of interest has been made and is within specifications. This in-line method is an alternative to off-line testing such as UV or HPLC reducing time and providing a more efficient process.

The present example describes real-time mid-IR technology deployed in mRNA manufacturing and in IVT and Drug Product unit operations using flow cell point of measurement. A mid-IR flow cell was engineered to be in series with Raman and UV-VIS flow cells in order to minimize the amount of sampling from unit operations. The use of flow cells is crucial to the operation of the PAT Box apparatus as each flow cell can be removed or added depending on the analytical needs of each unit operation, thereby providing modular capability of the apparatus.

For Mid-IR, optimization of the sequence of operations had to be resolved. Mid-IR require background spectral subtraction to highlight changes in the spectra. Selection of the background spectra according to the sequence of material addition to IVT was studied to improve Mid-IR post processing and modeling accuracy. The Mid IR flow cell needed to be installed in series with the Raman and UV-VIS flow cells to minimize the flow path length and minimize tubing length between flow cells thus minimizing hold up volume. As hold up volume increases, temperature differential between the external heat source (for example heat plate or vessel jacket) for the bioreactor and the internal reaction temperature due to the increased heat transfer lost through the recirculation tubing and thus increased the load on the external heat source. Increased hold up volume was also correlated to slower reaction kinetics in the reaction vessel. Therefore, it was imperative to maintain the shortest recirculation loop possible.

Example 4—Waters Multi Angle Light Scattering (MALS) Instrument

Figure 26:
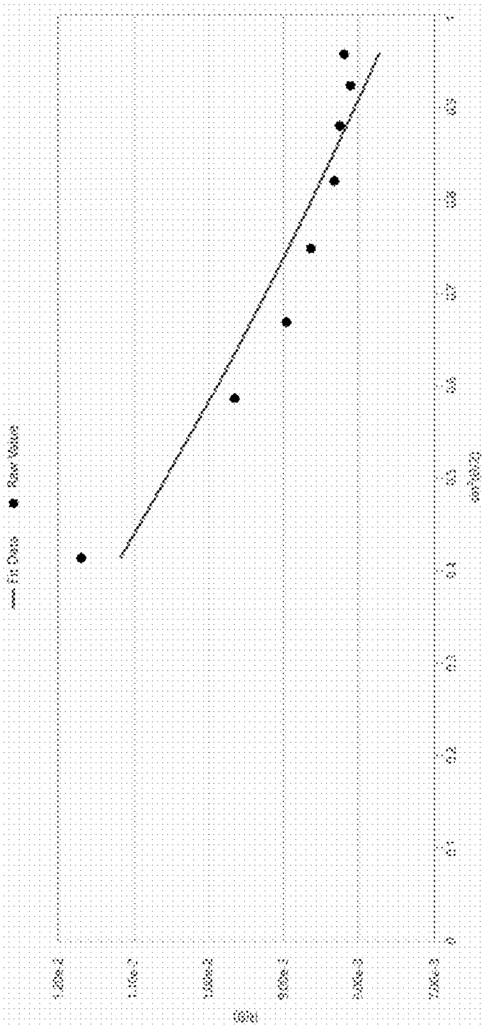
FIG. 26 illustrates results from Waters' MLAS system being used to measure particle average size, concentration, and Z-average radius for LNP samples.

In this example a MALS system is used to characterize lipid nanoparticles post LNP production. A sample was pulled from the LNP pool. FIG. 26 illustrates results from a Waters' MLAS system being used to obtain a correlation between the intensity of the scattered light and scattered light angle for the LNP samples.

The parameters for the MALS instrument were as follows:

7. Model—sphere
8. Particle RI Real—1.45
9. Particle RI Imaginary—0
10. Detectors—10, 12, 13, 14, 15, 16, 17, 18

The slice results indicated:

11. Slice index of 5.006
12. Particle concentration (1/mL) of 1.732E+11
13. Radius (nm) of 69.8

The region results indicated:

14. Region start—4.400
15. Region end—5.500
16. Average particle concentration (1/mL)—7.6E+9
17. Total number of particles—8.2E+10
18. Z—average radius (nm)—242

Figure 27:
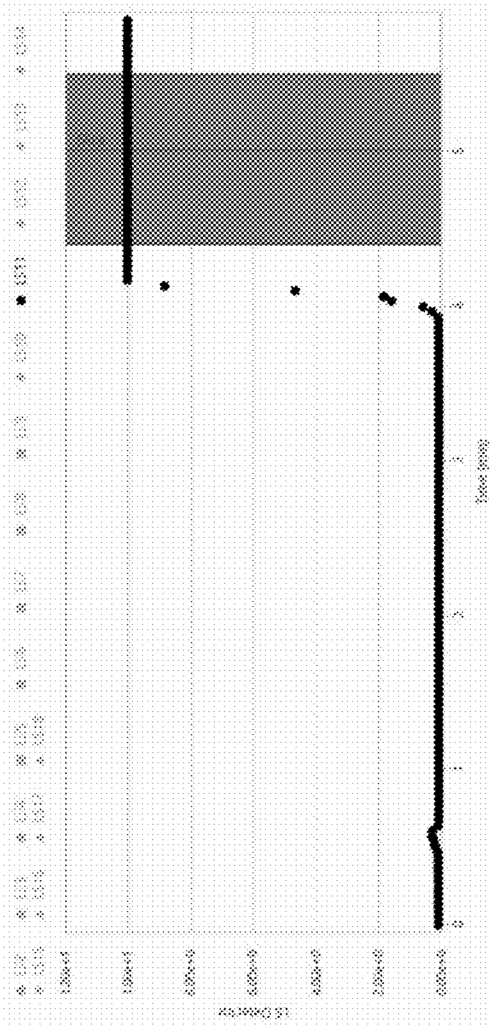
FIG. 27 illustrates a control graph of LS11.

FIG. 27 illustrates a control graph of LS11 that shows detection of particles by the instrument vs time of the measurement. These results were obtained by off-line measurements as a proof of concept. MALS represents another analytic that can be integrated in-line with the manufacturing process. MALS can be utilized with data-driven models to determine important CQAs during the LNP process, such as size, Pdi, and concentration) to support real-time and continuous manufacturing of LNPs. Off-line methods used to measure similar CQAs require hours and sometimes days to obtain results. As with other off-line analytics, during this time the process is on hold until results are obtained, which ultimately slows down production. Another important aspect of in-line analytics as described here is that is allows to track the reaction process and identify any anomalies (if they occur) in real-time, having the ability to control and react quicker reducing the risk of batch loss.

Example 5—in-Line DLS Instrument

This example characterized the ability of an in-line DLS instrument to measure CQAs relevant to lipid nanoparticles (LNP), including PDI and z-average in real-time (similar to MALS). Data for this step was gathered from a post LNP pool process step in the RNA manufacturing process.

Table 1 illustrates results from LSP NanoFlowSizer (in-line DLS):

| | Parameter | Value | Moving Average |
|---|---|---|---|
| 1 | Time (sec) | 10541.8 | |
| 2 | Number | 1766 | |
| 3 | Temperature | 25.7 | 25.7 |
| 4 | Z-average (nm) | 87 | 87 |
| 5 | Cumulant PDI | 0.33 | 0.33 |

Figure 29:
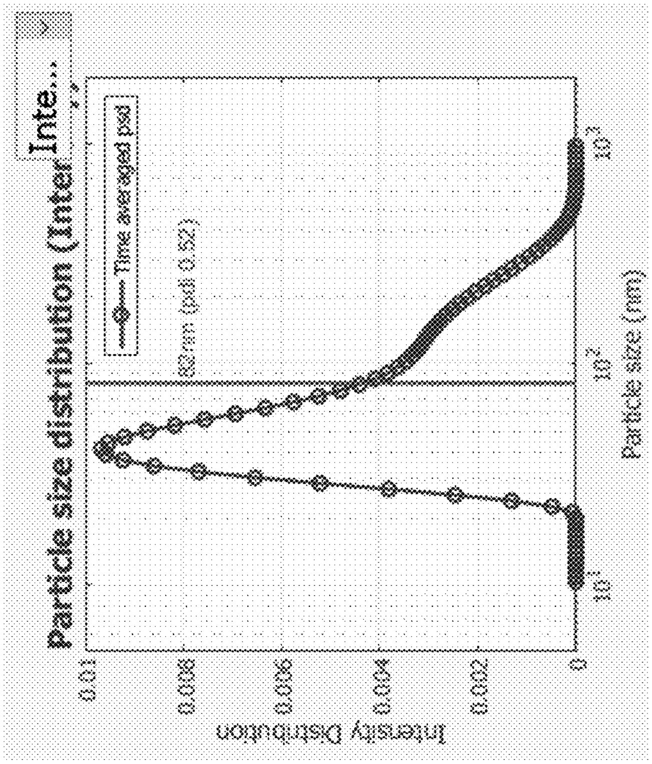
FIG. 29 illustrates results of a NanoFlowSizer being used to measure Z-average and PDI for the T3 LNP sample. The results are in good alignment with the off-line DLS measurement using Malvern systems.
Figure 28:
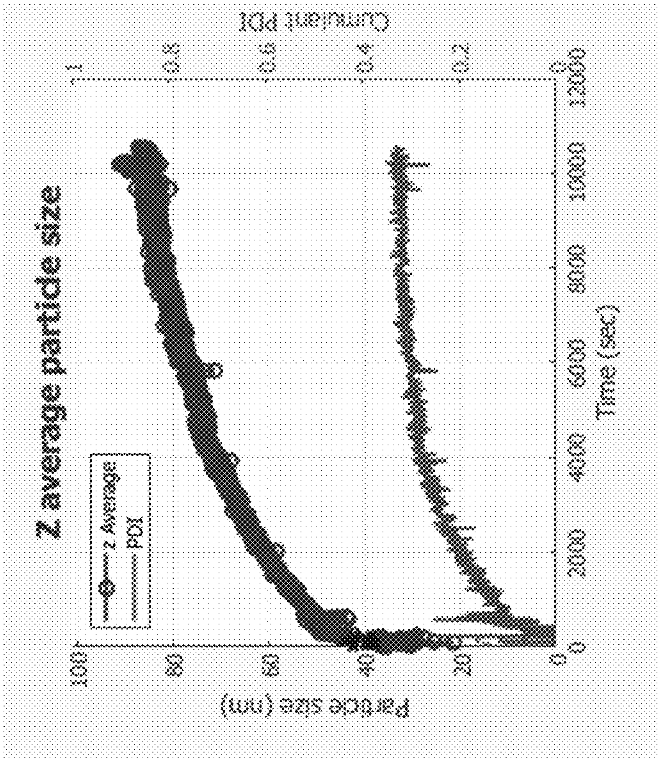
FIG. 28 illustrates results of a NanoFlowSizer being used to measure Z-average and polydispersity index (PDI) for the T2 LNP sample.

FIG. 28 is a graph of particle size versus time for the LNP sample as measured using a Z-average and polydispersity index (PDI). FIG. 29 is a graph showing the measure particle size distribution for the T3 LNP sample, as measured by DLS.

Figure 30:
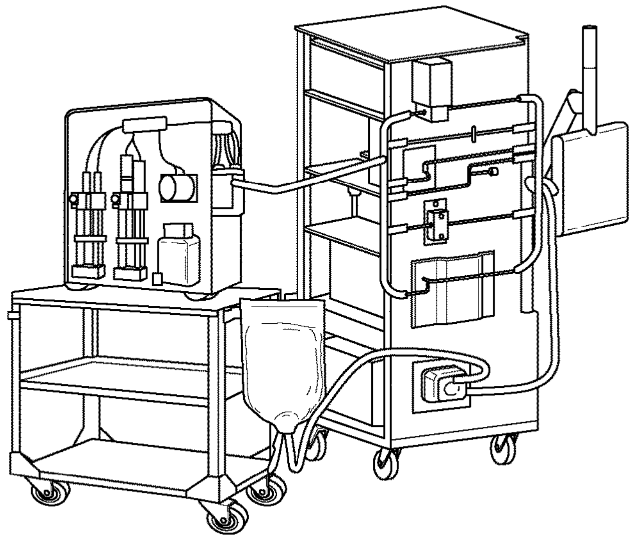
FIG. 30 illustrates a PAT Box Apparatus monitoring a bioprocess product flow stream.

FIG. 30 illustrates a PAT Box Apparatus monitoring a bioprocess product flow stream. The apparatus is situated directly on a unit op outlet monitoring real time quality attributes as the process fluid flows into an intermediate collection container. This illustrates the set-up of MALS with the LNP mixing skid outlet process flow stream and the data demonstrated in Example 4 to measure mRNA-LNP particle size, PDI, and particle concentration.

Figure 31:
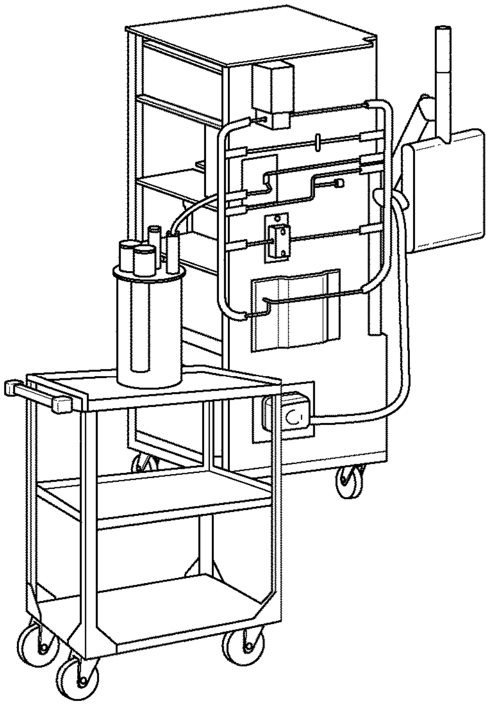
FIG. 31 illustrates a PAT Box Apparatus monitoring quality attributes and reaction kinetics of bioprocess reaction vessel containing reagents and buffer that produce active product ingredients and/or drug substances.

FIG. 31 illustrates a PAT Box Apparatus monitoring quality attributes and reaction kinetics of bioprocess reaction vessel containing reagents and buffer that produce active product ingredients and/or drug substances. This illustrates the set-up of Raman with the IVT reaction vessel to measure mRNA growth kinetics and NTP consumption kinetics and the data demonstrated in Example 1. This also illustrates the set-up of Mid IR with the IVT reaction vessel and the data demonstrated in Example 3 to measure mRNA concentration (mg/mL).

Figure 32:
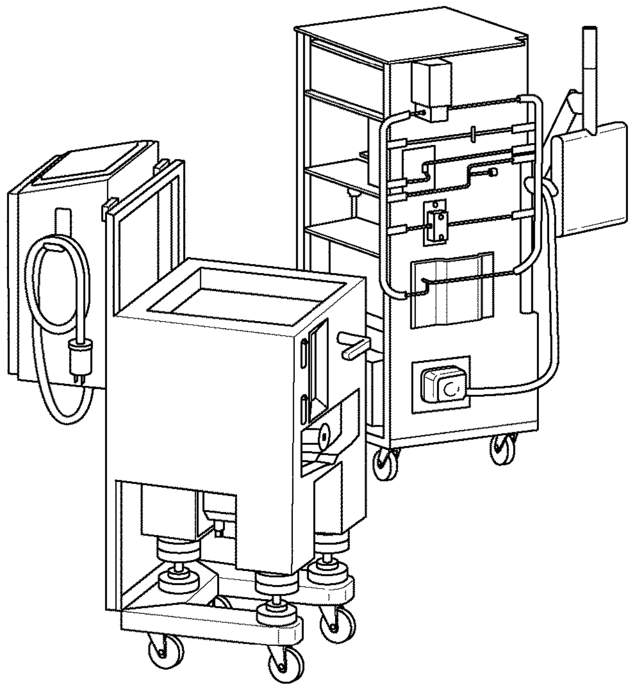
FIG. 32 illustrates PAT Box Apparatus monitoring quality attributes of a bioprocess product intermediate bulk in a surge vessel or other intermediate holding container typically positioned between unit operations.

FIG. 32 illustrates PAT Box Apparatus monitoring quality attributes of a bioprocess product intermediate bulk in a surge vessel or other intermediate holding container typically positioned between unit operations. This illustrates the set-up of Raman with the IVT pool vessel, TFF1 pool vessel, and TFF 2 pool vessel and the data demonstrated in Example 1 to measure mRNA concentration (mg/mL). This also illustrates the set-up of FlowVPX (UV spectrophotometer) with the TFF1 pool vessel, OligodT Chromatography pool vessel, and TFF 2 pool vessel and the data demonstrated in Example 2 to measure mRNA concentration (mg/mL). This also illustrates the set-up of MALS with the LNP pool vessel and the data demonstrated in Example 4 to measure mRNA-LNP particle size, PDI, and particle concentration. This also illustrates the set-up of In-line DLS with the LNP pool vessel and the data demonstrated in Example 5 to measure mRNA-LNP particle size, and PDI.

In the context of the foregoing, it was necessary to solve the technical problem of arranging all of the PAT instruments as close together as possible to create a compact modular unit adapted for moving quickly and easily between unit operations of the mRNA manufacturing process. The PAT instruments were placed in a stacked configuring which allowed for their respective flow cells to be connected either in series or in parallel. This configuration also permitted the inlet to the first flow cell and the outlet to the last flow cell to be more closely situated to the recirculation tubing connections to the surge vessel or reaction vessel, thus minimizing the recirculation loop length. As discussed above, minimizing recirculation loop length reduces hold up volume which minimizes quality implications to the IVT reactor in-process bulk. Reducing hold up also reduces yield loss and thus maximizes the value of the bioprocess fluid by reducing waste and reducing cost of goods.

The configuration of the PAT instruments into individually stacked decks also allows the PAT instruments to be added or removed quickly so that only the instrument(s) necessary to measure the CQAs at a particular unit operation are present in the apparatus. Removing unnecessary PAT instruments reduces capital cost and also reduces the stack height, thus minimizing the recirculation loop length and hold up volume. Being able to quickly reconfigure the PAT stack as needed per unit operation need also reduces downtime in the lab or cleanroom suite and maximizes the use of the operation space.

While the invention herein disclosed has been described by means of specific embodiments and applications thereof, numerous modifications and variations could be made thereto by those skilled in the art without departing from the scope of the invention set forth in the claims.

It will be appreciated that the present invention is set forth in various levels of detail in this application. In certain instances, details that are not necessary for one of ordinary skill in the art to understand the invention, or that render other details difficult to perceive may have been omitted. The terminology used herein is for the purpose of describing particular embodiments only and is not intended to be limiting beyond the scope of the appended claims. Unless defined otherwise, technical terms used herein are to be understood as commonly understood by one of ordinary skill in the art to which the disclosure belongs.

Various features of a process system may be used independently of, or in combination, with each other. It will be appreciated that a system as disclosed herein may be embodied in different forms and should not be construed as limited to the illustrated embodiments of the figures.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with one or more other features to yield a still further embodiment. Thus, it is intended that the present subject matter covers such modifications and variations as come within the scope of the appended claims and their equivalents.

In view of the above, it should be understood that the various embodiments illustrated in the figures have several separate and independent features, which each, at least alone, has unique benefits which are desirable for, yet not critical to, the presently disclosed vessel, system, and associated method. Therefore, the various separate features described herein need not all be present in order to achieve at least some of the desired characteristics and/or benefits described herein.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases “at least one”, “one or more”, and “and/or”, as used herein, are open-ended expressions that are both conjunctive and disjunctive in operation. The terms “a”, “an”, “the”, “first”, “second”, etc., do not preclude a plurality. For example, the term “a” or “an” entity, as used herein, refers to one or more of that entity. As such, the terms “a” (or “an”), “one or more” and “at least one” can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another.

In the claims, the term “comprises/comprising” does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A mobile, modular apparatus for deploying process analytical technology in a pharmaceutical or biopharmaceutical manufacturing process, the apparatus comprising a mobile platform with a weighted base, a control cabinet, and an instrument stack disposed within a housing comprising inlet and outlet ports, wherein the control cabinet comprises a human machine interface, a controller, and a data acquisition and analysis software layer and the instrument stack comprises two or more process analytical instruments and associated flow cells, a tubing assembly and valves; wherein each of the process analytical instruments is adapted to capture raw data indicative of at least one product attribute from a process fluid flowing through its associated flow cell;

wherein the inlet and outlet ports of the housing connect the flow cells via the tubing assembly in a recirculation loop to a flow path of at least one unit operation of the manufacturing process for in-line data acquisition and analysis; and wherein the controller is configured to execute instructions of the data acquisition and analysis software operate to automate operation of one or more valves between a vessel and the flow cells of the instrument stack to collect sample process fluid for the instrument stack, to process the raw data captured via the instrument stack with one or more models to determine or infer, in real-time, an indication of the at least one product attribute, and wherein the controller is configured to automate (i) a comparison of the indication of the at least one product attribute against a range for the attribute, ii) a determination of whether the indication is within the range, and iii) an initiation of a first action if the received indication is within the range or a second action if the indication is outside the range; and wherein the first action and the second action comprises actions configured to:

control a flow of the process fluid in the pharmaceutical or biopharmaceutical manufacturing process by operation of the valves for recirculating the process fluid through the instrument stack, releasing the process fluid through a material recycle flow path, releasing the process fluid through a waste flow path, or releasing the process fluid through a forward processing flow path.

2. The apparatus of claim 1, wherein the instrument stack comprises two or more spectroscopic instruments, optionally wherein the two or more spectroscopic instruments are selected from a Raman spectrophotometer, a mid-infrared (IR) spectrophotometer, a near-IR spectrophotometer, and an ultraviolet-visible (UV-VIS) spectrophotometer.

3. The apparatus of claim 1, wherein the instrument stack comprises a multiangle light scattering (MALS) detector.

4. The apparatus of claim 1, wherein the instrument stack comprises a Raman spectrophotometer, a UV-VIS spectrophotometer, a mid-infrared (IR) spectrophotometer, a near-IR spectrophotometer and a multiangle light scattering (MALS) detector.

5. The apparatus of claim 1, wherein the apparatus comprises an internal vessel in a form of a flexible or a rigid container defining an interior space suitable for holding a fluid, wherein the vessel includes inlet and outlet ports, an optional impeller for fluid recirculation, and an optional probe or sensor.

6. The apparatus of claim 1, wherein the apparatus comprises one or more environmental protections selected from electromagnetic frequency (EMF) shielding, vibrational dampening, shock absorption, and temperature control, optionally in a form of insulation.

7. The apparatus of claim 1, wherein the apparatus comprises at least one sample port or cuvette adapted to be connected to the recirculation loop of the flow path for at-line data acquisition and analysis.

8. The apparatus of claim 1, wherein the recirculation loop connecting the flow cells to the flow path of the at least one unit operation includes an external vessel.

9. The apparatus of claim 8, wherein the external vessel comprises a body in a form of a flexible or a rigid container defining an interior space, inlet and outlet ports, an optional impeller for fluid recirculation, and an optional probe or sensor.

10. The apparatus of claim 9, wherein the external vessel is a hold vessel, a release tank, a dilution tank, a mixing tank, or a stirred tank reactor.

11. The apparatus of claim 1, wherein the recirculation loop is connected via one or more valves to one or more of the material recycle flow path, the waste flow path, and the forward processing flow path.

12. The apparatus of claim 11, wherein the one or more valves is controlled by operation of the controller in accordance with one or more predetermined criteria.

13. The apparatus of claim 1, wherein the controller comprises an advanced process controller (APC).

14. The apparatus of claim 13, wherein the data acquisition and analysis layer includes multivariate data analysis, chemometric modeling and/or other advanced process modeling software.

15. A pharmaceutical or biopharmaceutical processing system comprising an apparatus as defined by claim 1 fluidly coupled to a unit operation of the pharmaceutical or biopharmaceutical manufacturing process in the recirculation loop.

16. The system of claim 15, wherein the apparatus is fluidly coupled in-line between the unit operation and a second unit operation in the process and the recirculation loop is connected via one or more valves to one or more of the material recycle flow path, the waste flow path, and the forward processing flow path.

17. The system of claim 15, wherein the apparatus is fluidly coupled in-line between the unit operations and a second unit operation in the process via an external vessel.

* * * * *